United States Patent
Pitterna et al.

(10) Patent No.: US 8,518,971 B2
(45) Date of Patent: Aug. 27, 2013

(54) INSECTICIDAL PHENYL- OR PYRIDYL-PIPERDINE COMPOUNDS

(75) Inventors: Thomas Pitterna, Stein (CH); Jerome Yves Cassayer, Stein (CH); Camilla Corsi, Stein (CH); Peter Maienfisch, Stein (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 148 days.

(21) Appl. No.: 13/055,204

(22) PCT Filed: Jul. 6, 2009

(86) PCT No.: PCT/EP2009/058482
§ 371 (c)(1),
(2), (4) Date: Jan. 21, 2011

(87) PCT Pub. No.: WO2010/009968
PCT Pub. Date: Jan. 28, 2010

(65) Prior Publication Data
US 2011/0136866 A1  Jun. 9, 2011

(30) Foreign Application Priority Data
Jul. 22, 2008 (GB) .................................. 0813436.3

(51) Int. Cl.
*A01N 43/40* (2006.01)
*C07D 401/12* (2006.01)
(52) U.S. Cl.
USPC ........................ 514/318; 546/193; 546/194
(58) Field of Classification Search
USPC .................. 546/193, 194; 514/318
See application file for complete search history.

(56) References Cited

FOREIGN PATENT DOCUMENTS
WO        2006/003494         1/2006

OTHER PUBLICATIONS
Marzabadi et al. "Preparation of . . . " CA140:357212 (2004).*
Acarine dictionary definition p. 1 (2012).*
Insect dictionary definition p. 1 (2012).*
Molluscs online definition p. 1 (2012).*
Nematode on line definition p. 1 (2012).*
Improper Markush training slide 66-67 (2011).*

* cited by examiner

*Primary Examiner* — Celia Chang
(74) *Attorney, Agent, or Firm* — Brian D. McAlhaney

(57) ABSTRACT

A compound of formula (I): wherein A, p, $R^1$, $R^3$, $R^4$, $R^5$, $R^6$, m, $R^7$, n and $R^8$ are as defined in claim 1. Furthermore, the present invention relates to intermediates used to prepare compounds of formula (I), to methods of using them to combat and control insect, acarine, nematode and mollusc pests and to insecticidal, acaricidal, nematicidal and molluscicidal compositions comprising them.

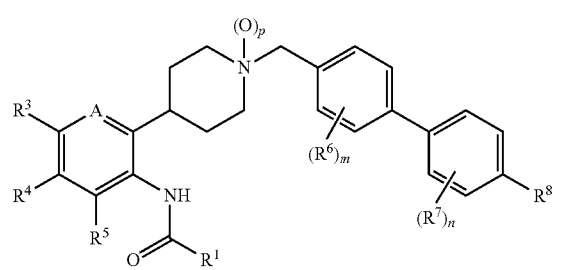

20 Claims, No Drawings

INSECTICIDAL PHENYL- OR PYRIDYL-PIPERDINE COMPOUNDS

This application is a 371 of International Application No. PCT/EP2009/058482 filed
Jul. 6, 2009, which claims priority to GB 0813436.3 filed Jul. 22, 2008, the contents of which are incorporated herein by reference.

The present invention relates to certain piperidine derivatives, to intermediates used to prepare them, to methods of using them to combat and control insect, acarine, nematode and mollusc pests and to insecticidal, acaricidal, nematicidal and molluscicidal compositions comprising them.

Piperidine derivatives with insecticidal properties are disclosed, for example, in WO 2006/003494.

It has now surprisingly been found that certain piperidine derivatives have enhanced insecticidal properties.

The present invention therefore provides a compound of formula (I):

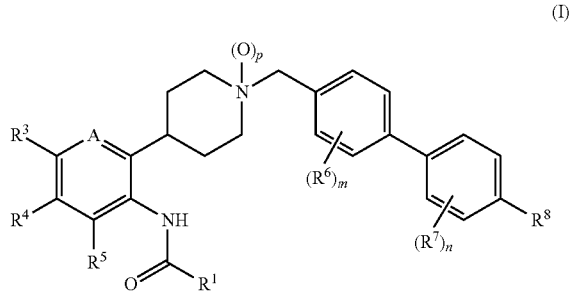

wherein
A is $CR^2$ or N;
p is 0 or 1;
$R^1$ is pyrid-4-yl optionally substituted by one or two substituents each independently selected from halogen, $C_1$-$C_3$alkyl or $C_1$-$C_3$haloalkyl;
$R^2$ is hydrogen, halogen, $C_1$-$C_3$haloalkyl or $C_1$-$C_3$haloalkoxy;
$R^3$ and $R^4$ are independently hydrogen, halogen, cyano, $C_1$-$C_8$alkyl, $C_1$-$C_8$haloalkyl, $C_2$-$C_8$alkenyl, $C_2$-$C_8$haloalkenyl, $C_3$-$C_8$cycloalkyl, $C_3$-$C_8$halocycloalkyl, $C_1$-$C_8$alkoxy, $C_1$-$C_8$haloalkoxy, $C_1$-$C_8$alkylthio or $C_1$-$C_8$haloalkylthio;
$R^5$ is hydrogen or halogen;
each $R^6$ and $R^7$ is independently halogen, $C_1$-$C_8$alkyl, $C_1$-$C_8$haloalkyl, $C_1$-$C_8$alkoxy or $C_1$-$C_8$haloalkoxy;
m is 0, 1 or 2;
n is 0, 1 or 2; and
$R^8$ is hydrogen, halogen, cyano, $C_1$-$C_8$alkyl, $C_1$-$C_8$haloalkyl, $C_3$-$C_8$cycloalkyl, $C_2$-$C_8$alkenyl, $C_2$-$C_8$haloalkenyl, $C_2$-$C_8$alkynyl, $C_1$-$C_8$alkoxy or $C_1$-$C_8$haloalkoxy; or a salt thereof.

The compounds of formula (I) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy or alkylthio) is a straight or branched chain and is, for example, methyl, ethyl, n-propyl, iso-propyl, n-butyl, sec-butyl, iso-butyl or tert-butyl. The alkyl groups are preferably $C_1$-$C_6$, more preferably $C_1$-$C_4$ and most preferably $C_1$-$C_3$ alkyl groups.

Alkenyl and alkynyl moieties can be in the form of straight or branched chains, and the alkenyl moieties, where appropriate, can be of either the (E)- or (Z)-configuration. Examples are vinyl, allyl and propargyl. The alkenyl and alkynyl groups are preferably $C_2$-$C_6$, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CH_2CF_3$ or —$CH_2CHF_2$.

Haloalkenyl groups are alkenyl groups which are substituted with one or more of the same or different halogen atoms and are, for example, —CH=$CF_2$ or —CCl=CClF.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methyl-cyclopropyl, 2-methyl-cyclopropyl, cyclobutyl, cyclopentyl and cyclohexyl.

Halocycloalkyl groups are cycloalkyl groups which are substituted with one or more of the same of different halogen atoms and may optionally be substituted by one or more methyl groups. Examples of monocyclic halocycloalkyl groups are 2,2-dichloro-cyclopropyl, 2,2-dichloro-1-methyl-cyclopropyl and 2-chloro-4-fluoro-cyclohexyl.

Salts comprise a charged version of a compound of formula (I) and a counter ion of the opposite charge. The compounds of formula (I) can have a positive charge, for example, on the nitrogen atom in the piperidine ring, if the nitrogen atom is quarternised by protonation with an organic or inorganic acid. Suitable organic acids include butylsulfonic acid, 2-chloro-benzoic acid, ethylsulfonic acid, 3-hydroxypropanesulfonic acid, 4-methylbenzenesulfonic acid, methanesulfonic acid, 3-phenoxy-propionic acid, tridecanoic acid and trifluoroacetic acid. Suitable inorganic acids include hydrochloric acid and phosphoric acid.

N-oxides are compounds of formula (I) where a nitrogen atom has been oxidised. In particular, N-oxides are compounds of formula (I) where the nitrogen atom in the piperidine ring has been oxidised. Oxidising agents which can convert a compound of formula (I) into the N-oxide of formula (I) include aqueous hydrogen peroxide.

Preferred groups and values for $R^1$, $R^2$, $R^3$, $R^4$, $R^5$, $R^6$, m, $R^7$, n and $R^8$ in any combination thereof are set out below.

Preferably $R^1$ is pyrid-4-yl optionally substituted by one or two substituents each independently selected from fluoro, chloro, bromo, methyl, difluoromethyl, chloro-difluoromethyl or trifluoromethyl; more preferably $R^1$ is pyrid-4-yl optionally substituted by one or two substituents each independently selected from fluoro, chloro or methyl; most preferably $R^1$ is pyrid-4-yl substituted by one or two substituents each independently selected from fluoro or chloro. It is preferred that one substituent occupies the 2-position of the pyrid-4-yl ring and that optionally a second substituent occupies the 5- or 6-position of the pyrid-4-yl ring. Examples of most preferred $R^1$ groups include 2-fluoro-pyrid-4-yl, 2-chloro-pyrid-4-yl, 2,5-dichloro-pyrid-4-yl, and 2,6-dichloro-pyrid-4-yl.

Preferably $R^2$ is hydrogen or halogen.
More preferably $R^2$ is hydrogen, fluoro or chloro.
Even more preferably $R^2$ is hydrogen or fluoro.
Most preferably $R^2$ is hydrogen.

Preferably $R^3$ is hydrogen, halogen, cyano, $C_1$-$C_6$alkyl, $C_1$-$C_6$haloalkyl, $C_2$-$C_6$alkenyl, $C_3$-$C_6$cycloalkyl, $C_1$-$C_6$alkoxy, $C_1$-$C_6$haloalkoxy, $C_1$-$C_6$alkylthio or $C_1$-$C_6$haloalkylthio.

More preferably $R^3$ is hydrogen, fluoro, chloro, bromo, cyano, methyl, iso-propyl, fluoromethyl, difluoromethyl, trifluoromethyl, heptafluoro-iso-propyl, vinyl, cyclopropyl, methoxy, ethoxy, difluoromethoxy, trifluoromethoxy, 2,2,2-trifluoroethoxy or trifluoromethylthio.

Even more preferably $R^3$ is hydrogen, fluoro, chloro, bromo, difluoromethyl, trifluoromethyl, heptafluoro-iso-propyl, vinyl, cyclopropyl, methoxy, difluoromethoxy, trifluoromethoxy or 2,2,2-trifluoroethoxy.

Yet even more preferably $R^3$ is hydrogen, fluoro, chloro, bromo, trifluoromethyl, cyclopropyl or trifluoromethoxy.

Most preferably $R^3$ is trifluoromethyl.

Preferably $R^4$ is hydrogen, halogen, cyano, $C_1$-$C_6$alkyl, $C_1$-$C_6$haloalkyl, $C_2$-$C_6$alkenyl, $C_3$-$C_6$cycloalkyl, $C_1$-$C_6$alkoxy, $C_1$-$C_6$haloalkoxy, $C_1$-$C_6$alkylthio or $C_1$-$C_6$haloalkylthio.

More preferably $R^4$ is hydrogen, fluoro, chloro, bromo, methyl, iso-propyl, fluoromethyl, difluoromethyl, trifluoromethyl, heptafluoro-iso-propyl, vinyl, cyclopropyl, methoxy, ethoxy, difluoromethoxy, trifluoromethoxy or 2,2,2-trifluoroethoxy.

Even more preferably $R^4$ is hydrogen, fluoro, chloro, methyl or trifluoromethyl.

Most preferably $R^4$ is hydrogen.

Preferably $R^5$ is hydrogen, fluoro, chloro or bromo.

More preferably $R^5$ is hydrogen or fluoro.

Most preferably $R^5$ is hydrogen.

Preferably each $R^6$ is independently halogen, $C_1$-$C_6$alkyl or $C_1$-$C_6$alkoxy.

More preferably each $R^6$ is independently fluoro, chloro, methyl or methoxy.

Most preferably each $R^6$ is independently fluoro or chloro.

Preferably m is 0 or 1.

Most preferably m is 0.

Preferably each $R^7$ is independently halogen, $C_1$-$C_6$alkyl or $C_1$-$C_6$alkoxy. More preferably each $R^7$ is independently fluoro, chloro, methyl or methoxy.

Most preferably each $R^7$ is independently fluoro or chloro.

Preferably n is 0 or 1.

Most preferably n is 0.

Preferably $R^8$ is hydrogen, halogen, cyano, $C_1$-$C_6$alkyl, $C_1$-$C_6$haloalkyl, $C_3$-$C_6$cycloalkyl, $C_2$-$C_6$alkenyl, $C_2$-$C_6$haloalkenyl, $C_2$-$C_6$alkynyl, $C_1$-$C_6$alkoxy or $C_1$-$C_6$haloalkoxy.

More preferably $R^8$ is hydrogen, fluoro, chloro, bromo, cyano, methyl, trifluoromethyl, cyclopropyl, ethynyl, methoxy or trifluoromethoxy.

Even more preferably $R^8$ is fluoro, chloro, bromo, trifluoromethyl or trifluoromethoxy.

Yet even more preferably $R^8$ is fluoro, chloro or trifluoromethyl.

Most preferably $R^8$ is fluoro.

A preferred embodiment are compounds of formula (Ia) wherein $R^1$, $R^3$, $R^4$, $R^5$ and $R^8$ are as defined for a compound of formula (I), A is C—H, and m, n, and p are 0. The preferences for $R^1$, $R^3$, $R^4$, $R^5$ and $R^8$ are the same as set out for a compound of formula (I).

A preferred embodiment are compounds of formula (Ib) wherein $R^1$, $R^3$, $R^4$, $R^5$ and $R^8$ are as defined for a compound of formula (I), A is C—H, m and n are 0, and p is 1. The preferences for $R^1$, $R^3$, $R^4$, $R^5$ and $R^8$ are the same as set out for a compound of formula (I).

A preferred embodiment are compounds of formula (Ic) wherein $R^1$, $R^3$, $R^4$, $R^5$ and $R^8$ are as defined for a compound of formula (I), A is N, and m, n and p are 0. The preferences for $R^1$, $R^3$, $R^4$, $R^5$ and $R^8$ are the same as set out for a compound of formula (I).

A preferred embodiment are compounds of formula (Id) wherein $R^1$, $R^3$, $R^4$, $R^5$ and $R^8$ are as defined for a compound of formula (I), A is N, m and n are 0, and p is 1. The preferences for $R^1$, $R^3$, $R^4$, $R^5$ and $R^8$ are the same as set out for a compound of formula (I).

A preferred embodiment are compounds of formula (Ie) wherein $R^1$, $R^3$, $R^4$, $R^5$ and $R^8$ are as defined for a compound of formula (I), A is C—F, and m, n, and p are 0. The preferences for $R^1$, $R^3$, $R^4$, $R^5$ and $R^8$ are the same as set out for a compound of formula (I).

A preferred embodiment are compounds of formula (If) wherein A, $R^1$, $R^3$, $R^6$, m, $R^7$, n and $R^8$ are as defined for a compound of formula (I), $R^4$ and $R^5$ are H, and p is 0, provided that at least one of m or n is not 0. The preferences for $R^1$, $R^3$, $R^6$, m, $R^7$, n and $R^8$ are the same as set out for a compound of formula (I), except that at least one of m and n is not 0.

A preferred embodiment are compounds of formula (Ig) wherein $R^1$, $R^3$, $R^4$, $R^5$ and $R^8$ are as defined for a compound of formula (I) and A is C—F, m and n are 0, and p is 1. The preferences for $R^1$, $R^3$, $R^4$, $R^5$ and $R^8$ are the same as set out for a compound of formula (I).

A preferred embodiment are compounds of formula (Ih) wherein A, $R^1$, $R^3$, $R^6$, m, $R^7$, n and $R^8$ are as defined for a compound of formula (I), $R^4$ and $R^5$ are H, and p is 1, provided that at least one of m or n is not 0. The preferences for $R^1$, $R^3$, $R^6$, m, $R^7$, n and $R^8$ are the same as set out for a compound of formula (I), except that at least one of m and n is not 0.

A preferred embodiment are salts of formula (Ij) wherein $R^1$, $R^3$, $R^4$, $R^5$ and $R^8$ are as defined for a compound of formula (I), A is C—H, m and n are 0, p is 1, and HX is selected from 2-chlorobenzoic acid, ethane sulfonic acid, hydrochloric acid, 3-hydroxypropane-1-sulfonic acid, methane sulfonic acid, (4-methylphenyl) sulfonic acid, 3-phenoxy-propionic acid, phosphoric acid, tridecanoic acid, trifluoroacetic acid. The preferences for $R^1$, $R^3$, $R^4$, $R^5$ and $R^8$ are the same as set out for a compound of formula (I).

A preferred embodiment are salts of formula (Ik) wherein $R^1$, $R^3$, $R^4$, $R^5$ and $R^8$ are as defined for a compound of formula (I), HX is defined as for a compound of formula (Ij), A is N, m and n are 0, and p is 1. The preferences for $R^1$, $R^3$, $R^4$, $R^5$ and $R^8$ are the same as set out for a compound of formula (I).

A preferred embodiment are salts of formula (Im) wherein $R^1$, $R^3$, $R^4$, $R^5$ and $R^8$ are as defined for a compound of formula (I), HX is defined as for a compound of formula (Ij), A is N, and m, n and p are 0. The preferences for $R^1$, $R^3$, $R^4$, $R^5$ and $R^8$ are the same as set out for a compound of formula (I).

Certain intermediates are novel and as such form a further aspect of the invention. One such group of intermediates are compounds of formula (II)

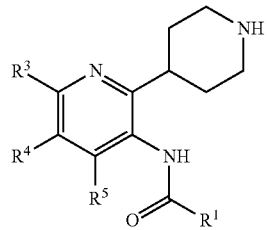

wherein $R^1$, $R^3$, $R^4$ and $R^5$ are defined as for a compound of formula (I). The preferences for $R^1$, $R^3$, $R^4$ and $R^5$ are the same as set out for a compound of formula (I).

Another group of intermediates are compounds of formula (III)

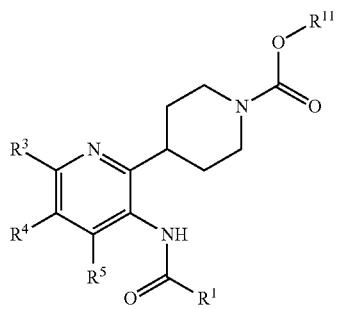

(III)

wherein $R^1$, $R^3$, $R^4$ and $R^5$ are defined as for a compound of formula (I); and $R^{11}$ is $C_1$-$C_6$alkyl, such as tert-butyl, $C_2$-$C_6$alkenyl, such as allyl, or benzyl optionally substituted with one to three substituents independently selected from halogen, $C_1$-$C_6$alkyl, $C_1$-$C_6$haloalkyl, $C_1$-$C_6$alkoxy or $C_1$-$C_6$haloalkoxy. The preferences for $R^1$, $R^3$, $R^4$ and $R^5$ are the same as set out for a compound of formula (I). $R^{11}$ is preferably tent-butyl.

Another group of intermediates are compounds of formula (IV)

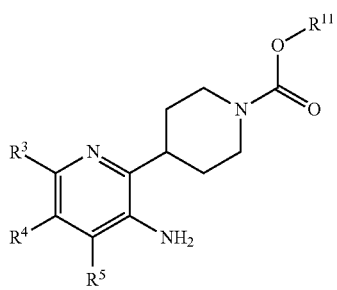

(IV)

wherein $R^3$, $R^4$ and $R^5$ are defined as for a compound of formula (I), or $R^3$ and $R^5$ are hydrogen and $R^4$ is fluoro, chloro or trifluoromethyl; and $R^{11}$ is defined as for a compound of formula (III). The preferences for $R^3$, $R^4$ and $R^5$ are the same as set out for a compound of formula (I). The preference for $R^{11}$ is the same as set out for a compound of formula (III).

Another group of intermediates are compounds of formula (V)

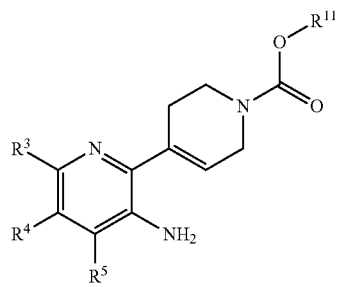

(V)

wherein $R^3$, $R^4$ and $R^5$ are defined as for a compound of formula (I), or $R^3$ and $R^5$ are hydrogen and $R^4$ is fluoro, chloro or trifluoromethyl; and $R^{11}$ is defined as for a compound of formula (III). The preferences for $R^3$, $R^4$ and $R^5$ are the same as set out for a compound of formula (I). The preference for $R^{11}$ is the same as set out for a compound of formula (III).

Another group of intermediates are compounds of formula (VI)

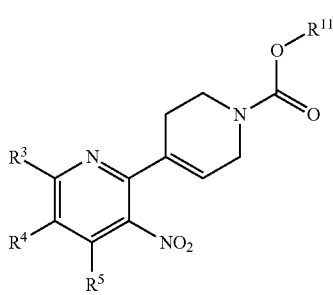

(VI)

wherein $R^3$, $R^4$ and $R^5$ are defined as for a compound of formula (I); and $R^{11}$ is as defined for a compound of formula (III). The preferences for $R^3$, $R^4$ and $R^5$ are the same as set out for a compound of formula (I). The preference for $R^{11}$ is the same as set out for a compound of formula (III).

The compounds of the invention may be made by a variety of methods as mentioned in WO 2006/003494. For example, compounds of formula (I) may be prepared according to Schemes 1, 2 and 3.

Thus a compound of formula (I) wherein A, $R^1$, $R^3$, $R^4$, $R^5$, $R^6$, m, $R^7$, n and $R^8$ are as defined for a compound of formula (I), may be obtained from a compound of formula (2) wherein A, $R^1$, $R^3$, $R^4$ and $R^5$ are as defined for a compound of formula (I), by reaction with a compound of formula (3) wherein $R^6$, m, $R^7$, n and $R^8$ is as defined for a compound of formula (I) and X is a leaving group, such as a halide (e.g. chloride, bromide or iodide) or a sulfonate (e.g. mesylate or tosylate), in the presence of a base, such as a tertiary amine (e.g. diisopropylethylamine or triethylamine), in an organic solvent, such as dichloromethane, acetonitrile or N,N-dimethylformamide, at a temperature of between 0° C. and 100° C., typically at ambient temperature, as shown in Scheme 1.

Scheme 1

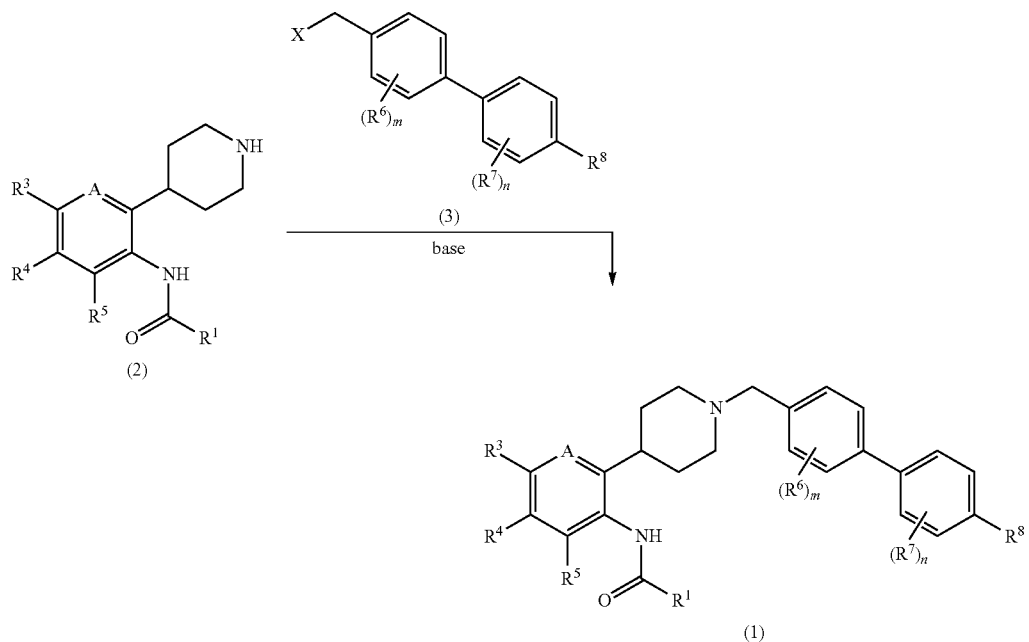

Alternatively, a compound of formula (I) as defined above, may be obtained from a compound of formula (2) as defined above, by reaction with an aldehyde of formula (4) wherein $R^8$ is as defined for a compound of formula (I) in the presence of a reducing agent, such as sodium (triacetoxy)borohydride, sodium cyanoborohydride or borane or the like, in an organic solvent, such as tetrahydrofuran, methanol or ethanol, at a temperature of between 0° C. and 100° C., typically at ambient temperature, as shown in Scheme 2.

Scheme 2

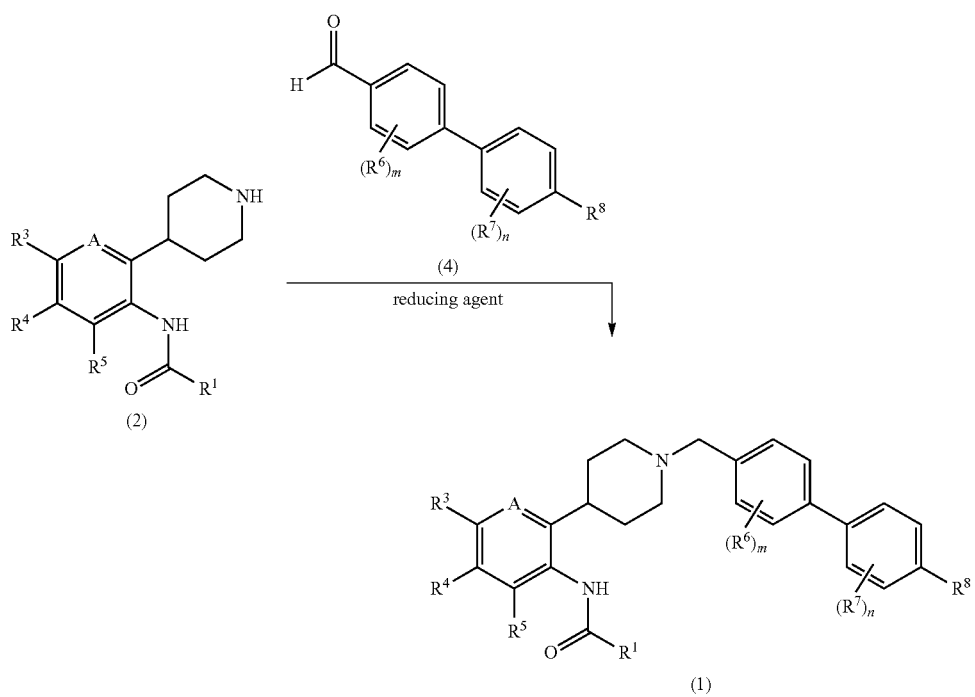

Compounds of formula (2) can be prepared as described in WO 2006/003494. Examples of these methods can be found in the preparation examples.

Compounds of formula (3) and (4) are either known compounds or may be prepared by methods known to a person skilled in the art. Examples of these methods can be found in the preparation examples.

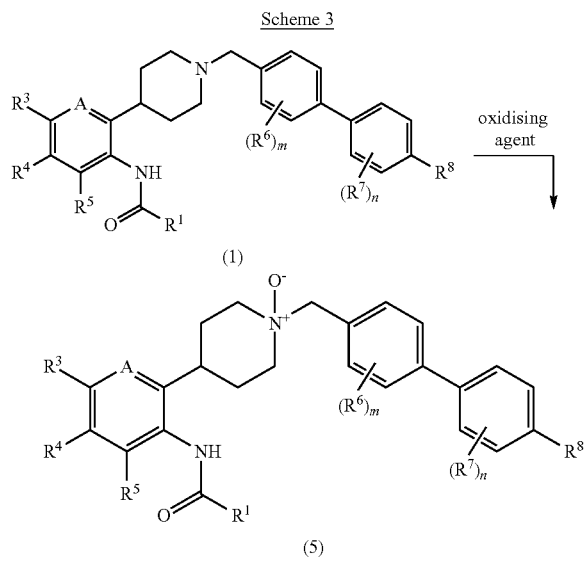

Scheme 3

N-oxides of formula (5) may be prepared by oxidation of a compound of formula (I) with an oxidising agent, such as hydrogen peroxide or 3-chloro-peroxybenzoic acid, in an organic solvent, such as dichloromethane, ethanol, methanol or water or mixtures of solvents, at a temperature of between −78° C. and 100° C., typically at ambient temperature, as shown in Scheme 3.

The compound of formula (I) have enhanced pesticidal properties. For example, the compounds may have increased insecticidal activity and/or improved photostability.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus*, *Reticulitermes flavipes*, *R. speratu*, *R. virginicus*, *R. hesperus*, and *R. santonensis*) and the *Termitidae* (for example *Globitermes* sulfureus), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

In a still further aspect the invention provides a method of combating and controlling pests at a locus which comprises treating the pests or the locus of the pests with an insecticidally, acaricidally, nematicidally or molluscicidally effective amount of a composition comprising a compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium hydrogencarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures suitably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, or spinosad, spinetoram or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, clothianidin, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine or pyrifluquinazon;

r) Spirotetramat, spirodiclofen or spiromesifen;

s) Flubendiamide, chloranthraliniprole, or cyanthraniliprole;

t) Cyenopyrafen or cyflumetofen; or u) Sulfoxaflor.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethylbenzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy) propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-diiso-propyl-5-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl(Z)-N-benzyl-N([methyl(methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples:

LCMS. Spectra were recorded on a ZMD (Micromass, Manchester UK) or a ZQ (Waters Corp. Milford, Mass., USA) mass spectrometer equipped with an electrospray source (ESI; source temperature 80 to 100° C.; desolvation temperature 200 to 250° C.; cone voltage 30 V; cone gas flow 50 l/hr, desolvation gas flow 400 to 600 l/hr, mass range: 150 to 1000 Da) and an Agilent 1100 HPLC (column: Gemini C18, 3 µm particle size, 110 Angstrom, 30×3 mm (Phenomenex, Torrance, Calif., USA); column temperature: 60° C.; flow rate 1.7 ml/min; eluent A: $H_2O$/HCOOH 100:0.05; eluent B: MeCN/MeOH/HCOOH 80:20:0.04; gradient: 0 min 5% B; 2-2.8 min 100% B; 2.9-3 min 5% B; UV-detection: 200-500 nm, resolution 2 nm. The flow was split post column prior to MS analysis. RT stands for retention time.

Alternatively, for compounds A25, A26, A27, A28, A27, C27 and C29, LC/MS method (Waters Alliance 2795 LC) with the following HPLC gradient conditions (Solvent A: 0.1% of formic acid in water and Solvent B: 0.1% of formic acid in acetonitrile) was used.

| Time (minutes) | A (%) | B (%) | Flow rate (ml/min) |
| --- | --- | --- | --- |
| 0 | 80 | 20 | 1.7 |
| 2.5 | 0 | 100 | 1.7 |
| 2.8 | 0 | 100 | 1.7 |
| 2.9 | 80 | 20 | 1.7 |

Type of column: Water atlantis dc18; Column length: 20 mm; Internal diameter of column: 3 mm; Particle Size: 3 micron; Temperature: 40° C.

EXAMPLE 1

This example illustrates the preparation of 2-chloro-N-{4,5-difluoro-2-[1-(4'-fluoro-biphenyl-4-ylmethyl)-piperidin-4-yl]-phenyl}-isonicotinamide (Compound A3 of Table A).

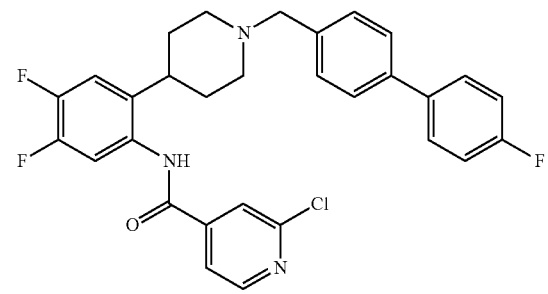 [SMILES: O=C(Nc1cc(F)c(F)cc1C1CCN(Cc2ccc(-c3ccc(F)cc3)cc2)CC1)c1ccnc(Cl)c1]

A mixture of 2-chloro-N-(4,5-difluoro-2-piperidin-4-yl-phenyl)-isonicotinamide (100 mg) (prepared according to procedures analogous to those described in WO 2006/003494), 4-chloromethyl-4'-fluoro-biphenyl (52.1 mg) (prepared as described in WO 2003/084916), and potassium carbonate (104 mg) in acetonitrile (10 ml) was stirred at 60° C. for 48 hours. The solvent was evaporated and the residue purified by chromatography on silica gel (eluent: ethyl acetate+1% methanol) to afford the title compound (100 mg) as a white amorphous solid. MS (ES+) 536/538 (MH+); $^1$H NMR (400 MHz, $CDCl_3$) 1.77 (m, 4H), 2.08 (m, 2H), 2.55 (m, 1H), 3.06 (m, 2H), 3.56 (s, 2H), 7.07-7.73 (m, 13H), 8.60 (d, 1H)

The following compounds were prepared according to procedures analogous to the procedure described in Example 1:

TABLE A

Compounds of formula (Ia)

(Ia)

| Comp No | R¹ | R³ | R⁴ | R⁵ | R⁸ | Physical state/ M.p. | HPLC (RT) | MS (ES+) |
|---|---|---|---|---|---|---|---|---|
| A1 | 2-chloro-pyrid-4-yl | H | —CH₃ | H | F | solid | 1.39 min | 514 |
| A2 | 2-chloro-pyrid-4-yl | F | F | F | F | solid | 1.42 min | 554 |
| A3 | 2-chloro-pyrid-4-yl | F | F | H | F | solid | 1.45 min | 536 |
| A4 | 2-chloro-pyrid-4-yl | H | —CF₃ | H | F | solid | 1.48 min | 568 |
| A5 | 2-chloro-pyrid-4-yl | F | H | H | F | solid | 1.37 min | 518 |
| A6 | 2-chloro-pyrid-4-yl | —OCF₃ | H | H | F | solid | 1.48 min | 584 |
| A7 | 2-chloro-pyrid-4-yl | —CF₃ | H | H | F | solid | 1.42 min | 568 |
| A8 | 2-chloro-pyrid-4-yl | —OCHF₂ | H | H | F | solid | 1.48 min | 566/568 |
| A9 | 2-fluoro-pyrid-4-yl | —OCHF₂ | H | H | F | solid | 1.31 min | 550 |
| A10 | 2,6-dichloro-pyrid-4-yl | —OCHF₂ | H | H | F | solid | 1.47 min | 600/602/604 |
| A11 | 2-chloro-pyrid-4-yl | —CF(CF₃)₂ | H | H | F | solid | 1.65 min | 668/670 |
| A12 | 2-chloro-pyrid-4-yl | Br | —CF₃ | H | F | solid | 1.65 min | 646/648/650 |
| A13 | 2-chloro-pyrid-4-yl | Cl | H | H | F | solid | 1.39 min | 534 |
| A14 | 2-chloro-pyrid-4-yl | Br | F | H | F | gum | 1.41 min | 596/598/600 |
| A15 | 2-chloro-pyrid-4-yl | Cl | F | H | F | 90-92° C. | 1.41 min | 552/554/556 |
| A16 | 2-chloro-pyrid-4-yl | H | Cl | H | F | solid | 1.38 min | 534 |
| A17 | 2-chloro-pyrid-4-yl | Cl | —CF₃ | H | F | solid | 1.50 min | 602/604/606 |
| A18 | 2-chloro-pyrid-4-yl | Br | F | Br | F | solid | 1.47 min | 674/676/678/680 |
| A19 | 2-chloro-pyrid-4-yl | F | —CF₃ | H | F | solid | 1.45 min | 586/588 |
| A20 | 2-chloro-pyrid-4-yl | —CF₃ | F | H | F | solid | 1.47 min | 586/588 |

TABLE A-continued

Compounds of formula (Ia)

(Ia)

| Comp No | R¹ | R³ | R⁴ | R⁵ | R⁸ | Physical state/ M.p. | HPLC (RT) | MS (ES+) |
|---|---|---|---|---|---|---|---|---|
| A21 | 2-fluoro-pyrid-4-yl | F | H | H | F | solid | 1.29 min | 502 |
| A22 | 2-bromo-pyrid-4-yl | F | H | H | F | solid | 1.34 min | 562 |
| A23 | 2,6-dichloro-pyrid-4-yl | F | H | H | F | solid | 1.42 min | 552 |
| A24 | 2-chloro-pyrid-4-yl | —CH=CH₂ | F | H | F | solid | 1.42 min | 544/546 |
| A25 | 2-chloro-pyrid-4-yl | F | H | H | —CF₃ | — | 1.28 min | 568.2 |
| A26 | 2-chloro-pyrid-4-yl | F | H | H | H | — | 1.15 min. | 500.2 |
| A27 | 2-chloro-pyrid-4-yl | F | H | H | Cl | — | 1.21 min | 534.2 |
| A28 | 2-chloro-pyrid-4-yl | F | H | H | —CH₃ | — | 1.17 min. | 514.2 |
| A29 | 2-chloro-pyrid-4-yl | F | H | H | Br | — | 1.25 min. | 578.1 |
| A30 | 2-chloro-pyrid-4-yl | cyclopropyl | F | H | F | solid | 1.46 min | 558/560 |
| A31 | 2-chloro-pyrid-4-yl | —CF₃ | H | H | Cl | >250° C. | 1.50 min | 584/586 |
| A32 | 2-chloro-pyrid-4-yl | —CF₃ | H | H | —CF₃ | 167-171° C. | 1.54 min | 618/620 |
| A33 | 2,6-dichloro-pyrid-4-yl | Br | F | H | F | 87-89° C. | 1.53 min | 630/632/634/636 |
| A34 | 2-chloro-pyrid-4-yl | —OCF₃ | Cl | H | F | 64-68° C. | 1.54 min | 618/620/622 |
| A35 | 2-chloro-pyrid-4-yl | F | Cl | H | F | 49-53° C. | 1.43 min | 552/554 |
| A36 | 2-chloro-pyrid-4-yl | —CF₃ | H | H | —OCH₃ | 150-152° C. | 1.44 min | 580/582 |
| A37 | 2-chloro-pyrid-4-yl | —CF₃ | Cl | H | F | 165-167° C. | 1.52 min | 602/604 |
| A38 | 2-chloro-pyrid-4-yl | —SCF₃ | H | H | F | 59-63° C. | 1.52 min | 600/602 |
| A39 | 2-chloro-pyrid-4-yl | Cl | Cl | H | F | 71-73° C. | 1.43 min | 568/570/572/574 |

TABLE A-continued

Compounds of formula (Ia)

(Ia)

| Comp No | R¹ | R³ | R⁴ | R⁵ | R⁸ | Physical state/ M.p. | HPLC (RT) | MS (ES+) |
|---|---|---|---|---|---|---|---|---|
| A40 | 2-chloro-pyrid-4-yl | —CN | F | H | F | 162-165° C. | 1.36 min | 543/545 |
| A41 | 5-chloro-2-fluoro-pyrid-4-yl | —CF₃ | H | H | F | foam | 1.43 min | 586/588 |
| A42 | 2-chloro-5-fluoro-pyrid-4-yl | —CF₃ | H | H | F | foam | 1.43 min | 586/588 |
| A43 | 2-chloro-pyrid-4-yl | —CF₃ | H | H | —CN | 97-98° C. | 1.39 min | 575/577 |
| A44 | 2-chloro-pyrid-4-yl | —CF₃ | H | H | —OCF₃ | 80-81° C. | 1.49 min | 634/635/636 |
| A45 | 2-chloro-pyrid-4-yl | —CF₃ | H | H | Br | 80-81° C. | 1.52 min | 628/630 |
| A46 | 2-chloro-pyrid-4-yl | H | —OCF₃ | H | F | 104-105° C. | 1.46 min | 584/586 |
| A47 | 2-chloro-pyrid-4-yl | —CF₃ | H | H | —C≡CH | 80-81° C. | 1.48 min | 574/576 |
| A48 | 2-chloro-pyrid-4-yl | —CF₃ | H | H | -cyclo-propyl | 82-83° C. | 1.55 min | 590/592 |
| A49 | 2-chloro-6-propyl-pyrid-4-yl | —CF₃ | H | H | F | | 1.44 min | 610 |
| A50 | 2-chloro-6-ethyl-pyrid-4-yl | —CF₃ | H | H | F | | 1.37 min | 596 |
| A51 | 3-trifluoro-methyl-pyrid-4-yl | —CF₃ | H | H | F | | 1.18 min | 602 |
| A52 | pyrid-4-yl | —CF₃ | H | H | F | | 1.04 min | 534 |
| A53 | 2,5-difluoro-pyrid-4-yl | —CF₃ | H | H | F | 212° C. | 1.39 min | 581 |

EXAMPLE 2

This example illustrates the preparation of 2-chloro-N-{4,5-difluoro-2-[1-(4'-fluoro-biphenyl-4-ylmethyl)-1-oxy-piperidin-4-yl]-phenyl}-isonicotinamide (Compound B1 of Table B).

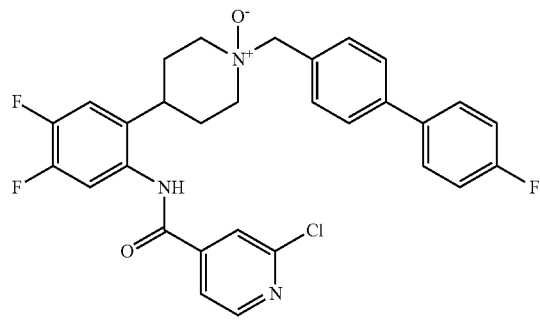 [SMILES: O=C(Nc1cc(F)c(F)cc1C1CC[N+]([O-])(Cc2ccc(-c3ccc(F)cc3)cc2)CC1)c1ccnc(Cl)c1]

A solution of 3-chloro-peroxybenzoic acid (21.6 mg) in dichloromethane (1 ml) was added dropwise to a solution of 2-chloro-N-{4,5-difluoro-2-[1-(4'-fluoro-biphenyl-4-ylmethyl)-piperidin-4-yl]-phenyl}-isonicotinamide (Example 1) (47 mg) in dichloromethane (5 ml) at −40° C. The solution was stirred at −40° C. for 1 hour, then warmed to 0° C. and quenched by addition of aqueous potassium carbonate (10% by weight) (3 ml). The mixture was extracted 3 times with dichloromethane. The combined organic extracts were dried over sodium sulfate and concentrated in vacuo to afford the title compound as an amorphous solid. MS (ES+) 552/554 (MH+); 1H NMR (400 MHz, MeOD) 1.80 (m, 2H), 2.40 (m, 2H), 2.93 (m, 1H), 3.23 (m, 2H), 3.48 (m, 2H), 4.44 (s, 2H), 7.18 (t, 2H), 7.28 (dd, 1H), 7.43 (dd, 1H), 7.64 (m, 6H), 7.83 (d, 1H), 7.95 (s, 1H), 8.56 (d, 1H).

The following compounds were prepared according to procedures analogous to the procedure described in Example 2:

TABLE B

Compounds of formula (Ib)

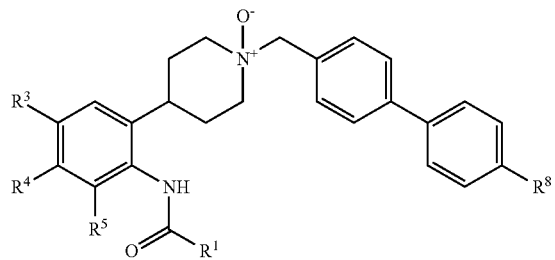

(Ib)

| Comp No | $R^1$ | $R^3$ | $R^4$ | $R^5$ | $R^8$ | Physical state/ M.p. | HPLC (RT) | MS (ES+) |
|---|---|---|---|---|---|---|---|---|
| B1 | 2-chloro-pyrid-4-yl | F | F | H | F | solid | 1.40 min | 552 |
| B2 | 2-chloro-pyrid-4-yl | H | —CF$_3$ | H | F | solid | 1.52 min | 584 |
| B3 | 2-chloro-pyrid-4-yl | F | F | F | F | solid | 1.48 min | 570 |
| B4 | 2-chloro-pyrid-4-yl | F | H | H | F | solid | 1.41 min | 534 |
| B5 | 2-chloro-pyrid-4-yl | —OCF$_3$ | H | H | F | solid | 1.47 min | 600 |
| B6 | 2-chloro-pyrid-4-yl | —CF$_3$ | H | H | F | solid | 1.48 min | 584 |
| B7 | 2-chloro-pyrid-4-yl | —OCHF$_2$ | H | H | F | solid | 1.41 min | 582/584 |
| B8 | 2-fluoro-pyrid-4-yl | —OCHF$_2$ | H | H | F | solid | 1.38 min | 566 |
| B9 | 2,6-dichloro-pyrid-4-yl | —OCHF$_2$ | H | H | F | solid | 1.60 min | 616/618/620 |
| B10 | 2-chloro-pyrid-4-yl | Br | —CF$_3$ | H | F | 192-194° C. | 1.54 min | 662/664/666 |

TABLE B-continued

Compounds of formula (Ib)

(Ib)

| Comp No | R¹ | R³ | R⁴ | R⁵ | R⁸ | Physical state/ M.p. | HPLC (RT) | MS (ES+) |
|---|---|---|---|---|---|---|---|---|
| B11 | 2-chloro-pyrid-4-yl | Br | F | H | F | 194-196° C. | 1.48 min | 612/614/616 |
| B12 | 2-chloro-pyrid-4-yl | Cl | F | H | F | 183-185° C. | 1.44 min | 568/570/572 |
| B13 | 2-chloro-pyrid-4-yl | Cl | H | H | F | solid | 1.42 min | 550 |
| B14 | 2-chloro-pyrid-4-yl | Cl | —CF₃ | H | F | solid | 1.54 min | 618/620/622 |
| B15 | 2-chloro-pyrid-4-yl | —CF(CF₃)₂ | H | H | F | 173-176° C. | 1.62 min | 684/686 |
| B16 | 2-chloro-pyrid-4-yl | Br | F | Br | F | 197-199° C. | 1.51 min | 690/692/694/696 |
| B17 | 2-chloro-pyrid-4-yl | F | —CF₃ | H | F | 198-200° C. | 1.49 min | 602/604 |
| B18 | 2-chloro-pyrid-4-yl | —CF₃ | F | H | F | 178-180° C. | 1.50 min | 602/604 |
| B19 | 2-chloro-pyrid-4-yl | H | Cl | H | F | solid | 1.43 min | 550 |
| B20 | 2-chloro-pyrid-4-yl | —CH=CH₂ | F | H | F | 240-242° C. | 1.46 min | 560/562 |
| B21 | 2-chloro-pyrid-4-yl | —CF₃ | H | H | —CF₃ | 170-172° C. | 1.59 min | 634/636 |
| B22 | 2,6-dichloro-pyrid-4-yl | Br | F | H | F | 209-213° C. | 1.57 min | 648/650/652 |
| B23 | 2-chloro-pyrid-4-yl | cyclo-propyl | F | H | F | 191-195° C. | 1.50 min | 574/576 |
| B24 | 2-chloro-pyrid-4-yl | F | Cl | H | F | 184-187° C. | 1.48 min | 568/570/572 |
| B25 | 2-chloro-pyrid-4-yl | —CF₃ | Cl | H | F | 187-190° C. | 1.58 min | 618/620/622 |
| B26 | 2-chloro-pyrid-4-yl | —SCF₃ | H | H | F | 144-147° C. | 1.52 min | 616/618 |
| B27 | 2-chloro-pyrid-4-yl | Cl | Cl | H | F | 195-197° C. | 1.48 min | 584/586/588/590 |
| B28 | 5-chloro-2-fluoro-pyrid-4-yl | —CF₃ | H | H | F | 173-175° C. | 1.47 min | 602/604 |
| B29 | 2-chloro-5-fluoro-pyrid-4-yl | —CF₃ | H | H | F | 184-186° C. | 1.48 min | 602/604 |

TABLE B-continued

Compounds of formula (Ib)

(Ib)

[Structure shown: compound with R³, R⁴, R⁵ on one phenyl ring bonded to piperidine N-oxide, connected via CH₂ to biphenyl with R⁸; NH-C(=O)-R¹ substituent]

| Comp No | R¹ | R³ | R⁴ | R⁵ | R⁸ | Physical state/ M.p. | HPLC (RT) | MS (ES+) |
|---|---|---|---|---|---|---|---|---|
| B30 | 2-chloro-pyrid-4-yl | —CN | F | H | F | 175-179° C. | 1.44 min | 559/561 |

EXAMPLE 3

This example illustrates the preparation of 2-chloro-N-[1'-(4'-fluoro-biphenyl-4-ylmethyl)-6-trifluoromethyl-1',2',3',4',5',6'-hexahydro-[2,4]bipyridinyl-3-yl]-isonicotinamide (Compound C1 of Table C).

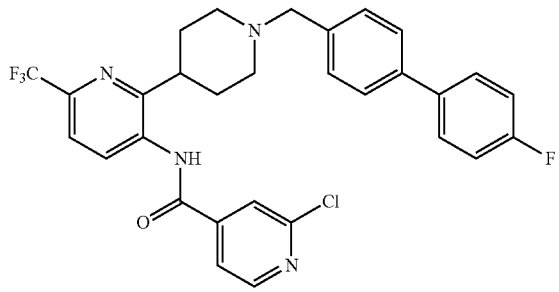 [SMILES: O=C(Nc1ccc(C(F)(F)F)nc1C1CCN(Cc2ccc(-c3ccc(F)cc3)cc2)CC1)c1ccnc(Cl)c1]

Step A: A solution of 3-amino-2-chloro-6-trifluoromethyl-pyridine (0.890 g), 4-(4,4,5,5-tetramethyl-[1,3,2]dioxaborolan-2-yl)-3,6-dihydro-2H-pyridine-1-carboxylic acid tert-butyl ester (1.4 g) (prepared as described in WO 2006/003494) and tetrakis(triphenyl-phosphine)palladium (0.200 g) in 1,2-dimethoxyethane (45 ml) was treated with aqueous potassium phosphate (1.1 M) (1.92 g). The reaction mixture was stirred at 80° C. for 3 hours. Aqueous workup with ethyl acetate furnished a residue which was purified by chromatography on silica gel (eluent: hexane/ethyl acetate 1:1) to give 3-amino-6-trifluoromethyl-3',6'-dihydro-2'H-[2,4]bipyridinyl-1'-carboxylic acid tert-butyl ester (1.5 g) as a white solid. MS (ES+) 288 (M-isoprene); 1H NMR (400 MHz, CDCl₃) 1.50 (s, 9H), 2.61 (m, 2H), 3.67 (t, 2H), 4.10 (m, 2H), 4.21 (s, 2H), 6.11 (s, 1H), 7.03 (d, 1H), 7.33 (d, 1H).

Step B: The compound obtained in Step A (1 g) was dissolved in ethanol (40 ml) and after degassing, palladium on charcoal (10% by weight) (100 mg) was added. Under a hydrogen atmosphere, the reaction mixture was stirred at ambient temperature for 2 days. Filtration on Celite® furnished 3-amino-6-trifluoromethyl-3',4',5',6'-tetrahydro-2'H-[2,4']bipyridinyl-1'-carboxylic acid tert-butyl ester (1 g) as white solid. MS (ES+) 290/292 (M-isoprene); 1H NMR (400 MHz, CDCl₃) 1.48 (s, 9H), 1.85 (m, 4H), 2.77 (m, 1H), 2.88 (m, 2H), 3.97 (s, 2H), 4.24 (m, 2H), 6.97 (d, 1H), 7.32 (d, 1H).

Step C: A solution of the compound obtained in Step C (1 g) in toluene (40 ml) was treated with N,N-diisopropylethylamine (1.05 ml) and then 2-chloro-isonicotinoyl chloride. The 2-chloro-isonicotinoyl chloride was prepared from 2-chloro-isonicotinic acid (0.496 g) and oxalyl chloride (0.346 ml) in dichloromethane (40 ml). The reaction mixture was stirred at ambient temperature for 2 hours, poured into aqueous sodium hydrogen carbonate (saturated), extracted with ethyl acetate, washed with water, dried over sodium sulfate and then concentrated in vacuo. The residue was purified by chromatography on silica gel (eluent: hexane/ethyl acetate 1:1) to afford 3-[(2-chloro-pyridine-4-carbonyl)-amino]-6-trifluoromethyl-3',4',5',6'-tetrahydro-2'H-[2,4]bipyridinyl-1'-carboxylic acid tert-butyl ester (1.1 g). MS (ES+) 485/487 (MH+), 429/431 (M-isoprene); 1H NMR (400 MHz, CDCl₃) 1.47 (s, 9H), 1.79 (m, 2H), 1.96 (m, 2H), 2.88 (m, 2H), 2.95 (m, 1H), 4.25 (m, 2H), 7.61 (d, 1H), 7.66 (m, 1H), 7.79 (s, 1H), 8.05 (s, 1H), 8.32 (d, 1H), 8.64 (d, 1H).

Step D: A solution of the compound obtained in Step C (300 mg) in dichloromethane (15 ml) was treated with trifluoroacetic acid (1.2 ml) at ambient temperature for 1 hour. Evaporation of the solvent and drying of the solid at high vacuum afforded 2-chloro-N-(6-trifluoromethyl-1',2',3',4',5',6'-hexahydro-[2,4]bipyridinyl-3-yl)-isonicotinamide trifluoroacetate. The free base was obtained by basic extraction (ethyl acetate, saturated aqueous hydrogen carbonate).

Step E:

Method A: A mixture of 2-chloro-N-(6-trifluoromethyl-1',2',3',4',5',6'-hexahydro-[2,4]bipyridinyl-3-yl)-isonicotinamide (150 mg), 4-chloromethyl-4'-fluoro-biphenyl (prepared as described in WO 2003/084916) (68 mg) and N,N-diisopropylethylamine (0.21 ml) in acetonitrile (10 ml) was stirred at ambient temperature for 16 hours. The solvent was evaporated and the residue purified by chromatography on silica gel (eluent: ethyl acetate) to afford the title compound (79 mg).

Method B: To a mixture of 2-chloro-N-(6-trifluoromethyl-1',2',3',4',5',6'-hexahydro-[2,4]bipyridinyl-3-yl)-isonicotinamide (3 g) (prepared as described in WO 2006/003494) and 4'-fluoro[1,1'-biphenyl]-4-carboxaldehyde (1.24 g) in tetrahydrofuran (120 ml) was added sodium (triacetoxy)borohydride (2 g) at ambient temperature. The reaction mixture was stirred at ambient temperature for 16 hours. The reaction mixture was quenched by addition of aqueous sodium hydrogen carbonate (saturated). The mixture was extracted with ethyl acetate. The organic extract was dried over sodium sulfate and concentrated in vacuo. The residue was purified by chromatography on silica gel (eluent: ethyl acetate) to afford the title compound as a solid (2.4 g).

2-Chloro-N-[1'-(4'-fluoro-biphenyl-4-ylmethyl)-6-trifluoromethyl-1',2',3',4',5',6'-hexahydro-[2,4]bipyridinyl-3-yl]-isonicotinamide: M.p. 63-66° C.; MS (ES+) 569/571 (MH+); 1H NMR (400 MHz, CDCl$_3$) 1.80 (m, 2H), 2.18 (m, 4H), 2.79 (m, 1H), 3.10 (m, 2H), 3.59 (s, 2H), 7.11 (m, 2H), 7.39-7.61 (m, 8H), 7.76 (s, 1H), 7.87 (bs, 1H), 8.45 (d, 1H), 8.64 (d, 1H).

EXAMPLE 4

This example illustrates the preparation of 2-chloro-N-[6-chloro-5-fluoro-1'-(4'-fluoro-biphenyl-4-ylmethyl)-1',2',3',4',5',6'-hexahydro-[2,4]bipyridinyl-3-yl]-isonicotinamide (Compound C17 of Table C).

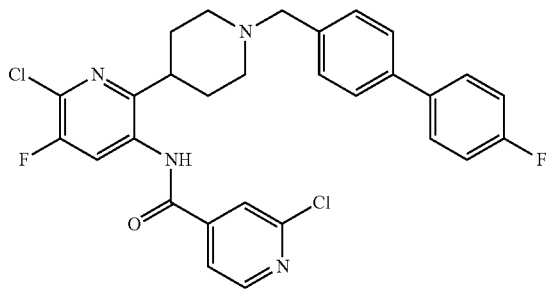 [SMILES: O=C(Nc1cc(F)c(Cl)nc1C1CCN(Cc2ccc(-c3ccc(F)cc3)cc2)CC1)c1ccnc(Cl)c1]

The title compound was prepared from 2-chloro-N-(6-chloro-5-fluoro-1',2',3',4',5',6'-hexahydro-[2,4']bipyridinyl-3-yl)-isonicotinamide as described in Step E of Example 3. 2-Chloro-N-(6-chloro-5-fluoro-1',2',3',4',5',6'-hexahydro-[2,4]bipyridinyl-3-yl)-isonicotinamide was prepared as follows:

Step A: A degassed solution of 2-chloro-5-fluoro-3-aminopyridine (3.5 g), 4-(4,4,5,5-tetramethyl-[1,3,2]dioxaborolan-2-yl)-3,6-dihydro-2H-pyridine-1-carboxylic acid tent-butyl ester (8.89 g) (prepared as described in WO 2006/003494) and bis(triphenylphosphine)palladium(II) chloride (0.84 g) in dioxane (157 ml) was treated with a degassed solution of sodium carbonate (7.6 g) in water (72 ml). The reaction mixture was stirred at reflux for 1 hour, cooled to ambient temperature and the solvent evaporated in vacuo. The residue was diluted with ethyl acetate, washed with water and brine, dried over sodium sulfate and concentrated in vacuo. Chromatography on silica gel (eluent: cyclohexane/ethyl acetate 8:2) afforded 3-amino-5-fluoro-3',6'-dihydro-2'H-[2,4]bipyridinyl-1'-carboxylic acid tert-butyl ester (4.6 g) as a solid. MS (ES+) 294 (MH+), 238 (M-isoprene); 1H NMR (400 MHz, CDCl$_3$) 1.48 (s, 9H), 2.53 (m, 2H), 3.64 (t, 2H), 3.99 (m, 2H), 4.08 (m, 2H), 5.99 (m, 1H), 6.70 (dd, 1H), 7.85 (d, 1H).

Step B: The compound obtained in Step A (4.4 g) was dissolved in ethanol (170 ml). Ammonium formate (9.4 g) and then palladium on charcoal (10% by weight) (1 g) were added. The reaction mixture was stirred at ambient temperature for 90 minutes, filtered through Celite® and the solvent removed in vacuo to afford 3-amino-5-fluoro-3',4',5',6'-tetrahydro-2'H-[2,4]bipyridinyl-1'-carboxylic acid tert-butyl ester (4.3 g) as a solid. MS (ES+) 296 (MH+), 240 (M-isoprene); 1H NMR (400 MHz, CDCl$_3$) 1.45 (s, 9H), 1.77 (m, 4H), 2.69 (m, 1H), 2.81 (m, 2H), 4.23 (m, 4H), 6.67 (dd, 1H), 7.85 (d, 1H).

Step C: A solution of the compound obtained in Step B (3.4 g) and N-chloro-succinimide (1.72 g) in N-methylpyrrolidinone (35 ml) was stirred at 110° C. for 1 hour. The reaction mixture was cooled to ambient temperature, poured into water and extracted several times with diethyl ether. The combined organic layers were washed with aqueous hydrochloric acid (dilute) and water, dried over sodium sulfate and then concentrated in vacuo. Chromatography on silica gel (eluent: cyclohexane/ethyl acetate 8:2) afforded 3-amino-5-fluoro-6-chloro-3',4',5',6'-tetrahydro-2'H-[2,4]bipyridinyl-1'-carboxylic acid tert-butyl ester (2.9 g) as a solid. MS (ES+) 330 (MH+), 274/276 (M-isoprene); 1H NMR (400 MHz, CDCl$_3$) 1.47 (s, 9H), 1.77 (m, 4H), 2.64 (m, 1H), 2.81 (m, 2H), 3.78 (m, 2H), 4.25 (m, 2H), 6.76 (d, 1H).

Step D: A solution of the compound obtained in Step C (2 g) in dichloromethane (100 ml) was treated with sodium hydrogen carbonate (5 g) and then 2-chloro-isonicotinoyl chloride. The 2-chloro-isonicotinoyl chloride was prepared from 2-chloro-isonicotinic acid (1.24 g) and oxalyl chloride (0.72 ml) in dichloromethane (100 ml). The reaction mixture was stirred at ambient temperature for 18 hours, poured into aqueous sodium hydrogen carbonate (saturated), extracted with dichloromethane, washed with water, dried over sodium sulfate and then concentrated in vacuo to afford 6-chloro-3-[(2-chloro-pyridine-4-carbonyl)-amino]-5-fluoro-3',4',5',6'-tetrahydro-2'H-[2,4]bipyridinyl-1'-carboxylic acid tert-butyl ester (2.2 g). MS (ES+) 369/371 (MH+-BOC).

Step E: A solution of the compound obtained in Step D (366 mg) in dichloromethane (10 ml) was treated with trifluoroacetic acid (0.6 ml) at ambient temperature for 1 hour 30 minutes. Evaporation of the solvent and precipitation from diethyl ether afforded 2-chloro-N-(6-chloro-5-fluoro-1',2',3',4',5',6'-hexahydro-[2,4]bipyridinyl-3-yl)-isonicotinamide trifluoroacetate.

EXAMPLE 5

This example illustrates the preparation of 2-chloro-N-[5,6-dichloro-1'-(4'-fluoro-biphenyl-4-ylmethyl)-1',2',3',4',5',6'-hexahydro-[2,4]bipyridinyl-3-yl]-isonicotinamide (Compound C2 of Table C).

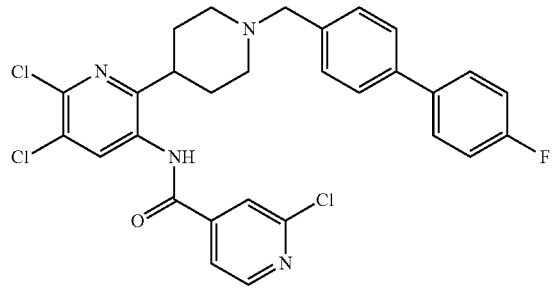 [SMILES: O=C(Nc1cc(Cl)c(Cl)nc1C1CCN(Cc2ccc(-c3ccc(F)cc3)cc2)CC1)c1ccnc(Cl)c1]

The title compound was prepared from 2-chloro-N-(5,6-dichloro-1',2',3',4',5',6'-hexahydro-[2,4]bipyridinyl-3-yl)-isonicotinamide according to procedures analogous to those described in Example 4 starting from 2,5-dichloro-3-amino-pyridine instead of 2-chloro-5-fluoro-3-amino-pyridine. Step B was replaced by the following procedure:

Step B': The tetrahydropyridine intermediate obtained in Step A (3 g) was hydrogenated in methanol (350 ml) at 80° C. and 100 bar hydrogen in the presence of 1,1'-bis(di-iso-propyl-phosphino)ferrocene(1,5-cyclooctadiene)rhodium(I) tetrafluoroborate (46 mg) for 21 hours to afford 3-amino-5- fluoro-3',4',5',6'-tetrahydro-2'H-[2,4]bipyridinyl-1'-carboxylic acid tert-butyl ester.

Alternatively, the latter intermediate can be obtained as described in WO 2006/003494 using a Negishi coupling between 2,5-dichloro-3-amino-pyridine and 4-iodo-piperidine 1-carboxylic acid tert-butyl ester.

EXAMPLE 6

This example illustrates the preparation of N-[6-bromo-5-fluoro-1'-(4'-fluoro-biphenyl-4-ylmethyl)-1',2',3',4',5',6'-hexahydro-[2,4]bipyridinyl-3-yl]-2-chloro-isonicotinamide (Compound C5 of Table C).

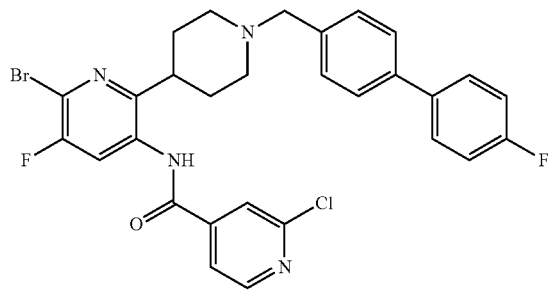

The title compound was prepared according to procedures analogous to those described in Example 4 replacing N-chlorosuccinimide by N-bromosuccinimide in Step C.

EXAMPLE 7

This example illustrates the preparation of 2-chloro-N-[6-chloro-1'-(4'-fluoro-biphenyl-4-ylmethyl)-5-methyl-1',2',3',4',5',6'-hexahydro-[2,4]bipyridinyl-3-yl]-isonicotinamide (Compound C16 of Table C).

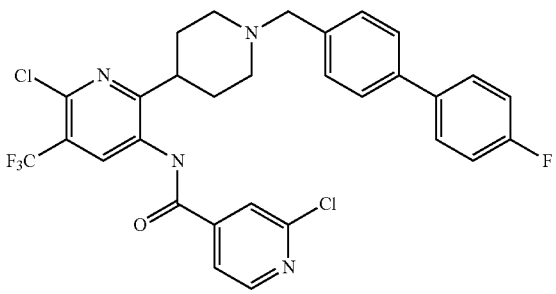 [SMILES: O=C(Nc1cc(C(F)(F)F)c(Cl)nc1C1CCN(Cc2ccc(-c3ccc(F)cc3)cc2)CC1)c1ccnc(Cl)c1]

The title compound was prepared according to procedures analogous to those described in Example 4 starting from 3-amino-2-chloro-5-trifluoromethyl-pyridine (prepared as described in EP 178260, EP 272824) instead of 2-chloro-5-fluoro-3-amino-pyridine.

Alternatively, the latter intermediate can be obtained directly via a Suzuki coupling using the conditions described in Example 3, between 3-amino-2,6-dichloro-5-trifluoro-methyl-pyridine and 4-(4,4,5,5-tetramethyl-[1,3,2]dioxaborolan-2-yl)-3,6-dihydro-2H-pyridine-1-carboxylic acid tent-butyl ester (prepared as described in WO 2006/003494) followed by a homogeneous catalytic hydrogenation as described for Example 5 (Step B').

The preparation of 3-amino-2,6-dichloro-5-trifluoromethyl-pyridine from 3-amino-2-chloro-5-trifluoromethyl-pyridine was as follows. A solution of 3-amino-2-chloro-5-trifluoromethyl-pyridine (5 g) (prepared as described in EP 178260, EP 272824) and N-chlorosuccinimide (3.7 g) in acetonitrile (125 ml) was stirred at ambient temperature for 16 hours. The reaction mixture was poured into water, extracted with ethyl acetate, dried over sodium sulfate and then concentrated in vacuo. Chromatography on silica gel (eluent: hexane/ethyl acetate 3:1) afforded 3-amino-2,6-dichloro-5-trifluoromethyl-pyridine (3.5 g): MS (ES+) 231/233/235 (MH+); 1H NMR (400 MHz, CDCl$_3$) 4.34 (s, 2H), 7.35 (s, 1H).

EXAMPLE 8

This example illustrates the preparation of 2-chloro-N-[6-bromo-1'-(4'-fluoro-biphenyl-4-ylmethyl)-5-methyl-1',2',3',4',5',6'-hexahydro-[2,4]bipyridinyl-3-yl]-isonicotinamide (Compound C15 of Table C).

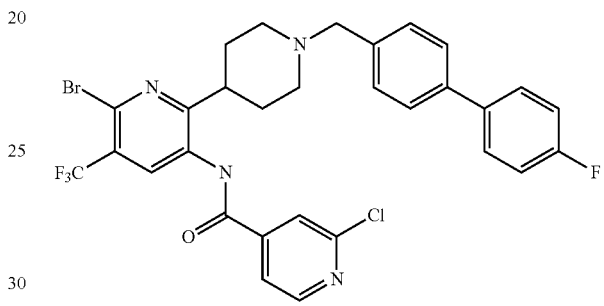

The title compound was prepared according to procedures analogous to those described in Example 7 replacing N-chlorosuccinimide by N-bromosuccinimide.

EXAMPLE 9

This example illustrates the preparation of 2-chloro-N-{4,5,6-trichloro-1'-(4'-fluoro-biphenyl-4-ylmethyl)-1',2',3',4',5',6'-hexahydro-[2,4]bipyridinyl-3-yl}-isonicotinamide (Compound C30 of Table C).

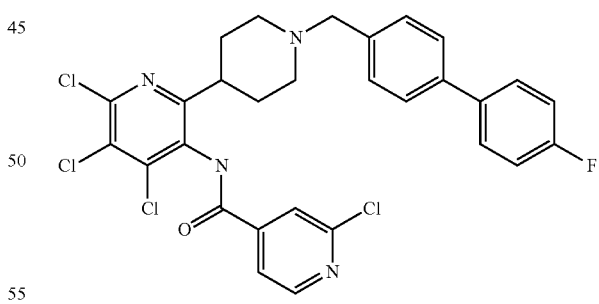

The title compound was prepared according to procedures analogous to those described in Example 5 using 2 equivalents of N-chlorosuccinimide in the chlorination step (Step C).

EXAMPLE 10

This example illustrates the preparation of 2-chloro-N-{1'-(4'-fluoro-biphenyl-4-ylmethyl)-4-fluoro-6-trifluoromethyl-1',2',3',4',5',6'-hexahydro-[2,4]bipyridinyl-3-yl}-isonicotinamide (Compound C41 of Table C).

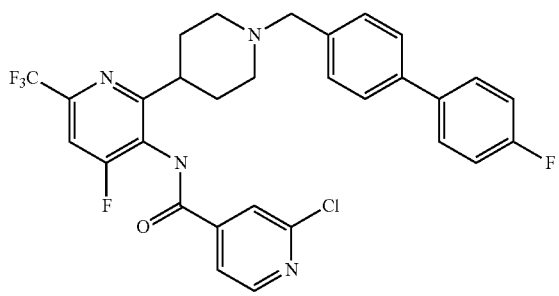 [SMILES: O=C(Nc1c(F)cc(C(F)(F)F)nc1C1CCN(Cc2ccc(-c3ccc(F)cc3)cc2)CC1)c1ccnc(Cl)c1]

Step A: A solution of the compound obtained in Step B of Example 3 (10.35 g) and N-chlorosuccinimide (4.4 g) in N-methylpyrrolidinone (150 ml) was stirred at ambient temperature for 2.5 hours. The reaction mixture was poured into water, and extracted several times with ethyl acetate. The combined organic layers were washed with brine, dried over sodium sulfate and then concentrated in vacuo. Chromatography on silica gel (eluent: hexane/ethyl acetate 1:1) afforded 3-amino-4-chloro-6-trifluoromethyl-3',4',5',6'-tetrahydro-2'H-[2,4]bipyridinyl-1'-carboxylic acid tent-butyl ester (9.6 g) as a foam. MS (ES+) 380/382 (MH+), 324/326 (M-isoprene); 1H NMR (400 MHz, CDCl$_3$) 1.48 (s, 9H), 1.85 (m, 4H), 2.82 (m, 3H), 4.24 (m, 2H), 4.41 (br s, 2H), 7.46 (s, 1H).

Step B: A solution of the compound obtained in Step A (7.6 g) and trifluoroacetic acid (61.7 ml) in dichloromethane (380 ml) was heated to 55° C. At this temperature, aqueous hydrogen peroxide (30% by weight) (23 ml) was slowly added over a period of 30 minutes. The reaction mixture was kept at this temperature for a further 2 hours. The reaction mixture was poured into water and extracted several times with dichloromethane. The combined organic layers were washed with brine, dried over sodium sulfate, and then concentrated in vacuo. The residue was re-dissolved in dichloromethane (200 ml). Di-tert-butyl-dicarbonate (5.4 g) and N,N-diisopropyl-ethylamine (14.2 ml) were subsequently added and the reaction mixture was stirred for 16 hours. The reaction mixture was quenched with water and extracted with dichloromethane. The combined organic layers were washed with brine, dried over sodium sulfate and then concentrated in vacuo. Chromatography on silica gel (eluent: hexane/ethyl acetate 5:1) afforded 4-chloro-3-nitro-6-trifluoromethyl-3',4',5',6'-tetrahydro-2'H-[2,4]bipyridinyl-1'-carboxylic acid tert-butyl ester (4.9 g) as a foam. MS (ES+) 410/412 (MH+), 354/356 (M-isoprene); 1H NMR (400 MHz, CDCl$_3$) 1.48 (s, 9H), 1.77 (m, 2H), 1.95 (m, 2H), 2.85 (m, 3H), 4.26 (m, 2H), 7.74 (s, 1H).

Step C: A solution of the compound obtained in Step B (1.2 g) and spray dried potassium fluoride (339 mg) in dimethyl sulfoxide (57 ml) was stirred at 80° C. for 1 hour. The reaction mixture was poured into water and extracted several times with ethyl acetate. The combined organic layers were washed with brine, dried over sodium sulfate and then concentrated in vacuo. Chromatography on silica gel (eluent: hexane/ethyl acetate 5:1) afforded 4-fluoro-3-nitro-6-trifluoromethyl-3',4',5',6'-tetrahydro-2'H-[2,4]bipyridinyl-1'-carboxylic acid tert-butyl ester (0.7 g) as a foam. MS (ES+) 338/339 (M-isoprene); 1H NMR (400 MHz, CDCl$_3$) 1.48 (s, 9H), 1.79 (m, 2H), 1.94 (m, 2H), 2.79 (m, 2H), 2.99 (m, 1H), 4.26 (m, 2H), 7.51 (d, 1H).

Step D: The compound obtained from Step C (1.8 g) was dissolved in ethanol (48 ml) and after degassing, palladium on charcoal (10% by weight) (500 mg) was added. Under a hydrogen atmosphere, the reaction mixture was stirred at ambient temperature for 1 day. Filtration on Celite® furnished 3-amino-4-fluoro-6-trifluoromethyl-3',4',5',6'-tetrahydro-2'H-[2,4']bipyridinyl-1'-carboxylic acid tert-butyl ester (1.6 g) as a white solid. MS (ES+) 364/365 (MH+), 308/309 (M-isoprene); 1H NMR (400 MHz, CDCl$_3$) 1.48 (s, 9H), 1.85 (m, 4H), 2.86 (m, 3H), 3.90 (br s, 2H), 4.25 (m, 2H), 7.22 (d, 1H).

The compound obtained in Step D was then treated according to the procedures described in Example 3 (Step C and Step D) to obtain the title compound.

EXAMPLE 11

This example illustrates the preparation of 2-chloro-N-{1'-(4'-fluoro-biphenyl-4-ylmethyl)-6-fluoro-5-trifluoromethyl-1',2',3',4',5',6'-hexahydro-[2,4]bipyridinyl-3-yl}-isonicotinamide (Compound C31 of Table C).

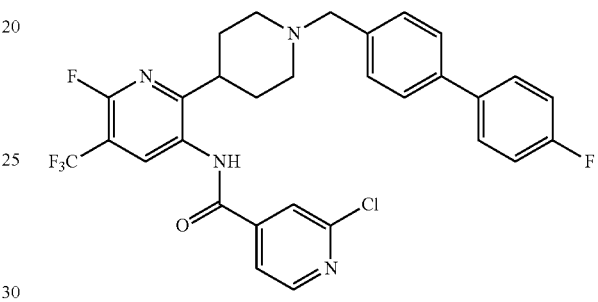

Step A: To a solution of the intermediate 3-amino-6-chloro-5-trifluoromethyl-3',4',5',6'-tetrahydro-2'H-[2,4]bipyridinyl-1'-carboxylic acid tert-butyl ester (4 g), obtained as described in Example 8 via Suzuki coupling followed by catalytic hydrogenation, in dichloromethane (200 ml), was added trifluoroacetic acid (32 ml). The solution was heated to 55° C. and at this temperature, aqueous hydrogen peroxide (30% by weight) (10.5 ml) was slowly added over a period of 30 minutes. The reaction mixture was kept at this temperature for a further 90 minutes before was poured into water and extracted several times with dichloromethane. The combined organic layers were washed with brine, dried over sodium sulfate and then concentrated in vacuo. The residue was re-dissolved in dichloromethane (110 ml). Di-tert-butyl-dicarbonate (3.5 g) and N,N-diisopropylethylamine (7.6 ml) were subsequently added and the reaction mixture was stirred for 16 hours at ambient temperature. The reaction mixture was quenched with water and extracted with dichloromethane. The combined organic layers were washed with brine, dried over sodium sulfate and then concentrated in vacuo. Chromatography on silica gel (eluent: hexane/ethyl acetate 10:1) afforded 6-chloro-3-nitro-5-trifluoromethyl-3',4',5',6'-tetrahydro-2'H-[2,4]bipyridinyl-1'-carboxylic acid tert-butyl ester (3 g) as a foam. MS (ES+) 410/412 (MH+), 354/356 (M-isoprene); 1H NMR (400 MHz, CDCl$_3$) 1.49 (s, 9H), 1.89 (m, 4H), 2.84 (m, 2H), 3.50 (m, 1H), 4.29 (m, 2H), 8.48 (s, 1H).

Step B: A solution of the compound obtained in Step A (2.5 g) and spray dried potassium fluoride (710 mg) in dimethyl sulfoxide (120 ml) was stirred at 80° C. for 40 minutes. The reaction mixture was poured into a mixture of ice and water and extracted several times with ethyl acetate. The combined organic layers were washed with brine, dried over sodium sulfate and then concentrated in vacuo. Chromatography on silica gel (eluent: hexane/ethyl acetate 5:1) afforded 6-fluoro-3-nitro-5-trifluoromethyl-3',4',5',6'-tetrahydro-2'H-[2,4]bipyridinyl-1'-carboxylic acid tert-butyl ester (1.13 g) as a foam. MS (ES+) 338/339 (M-isoprene); 1H NMR (400 MHz, CDCl$_3$) 1.48 (s, 9H), 1.90 (m, 4H), 2.84 (m, 2H), 3.53 (m, 1H), 4.29 (m, 2H), 8.57 (d, 1H).

The compound obtained in Step B was then treated according to the procedures described in Example 3 (Step B, Step C and Step D) to obtain the title compound.

EXAMPLE 12

This example illustrates the preparation of 2-chloro-N-{1'-(4'-fluoro-biphenyl-4-ylmethyl)-5,6-difluoro-1',2',3',4',5',6'-hexahydro-[2,4]bipyridinyl-3-yl}-isonicotinamide (Compound C25 of Table C).

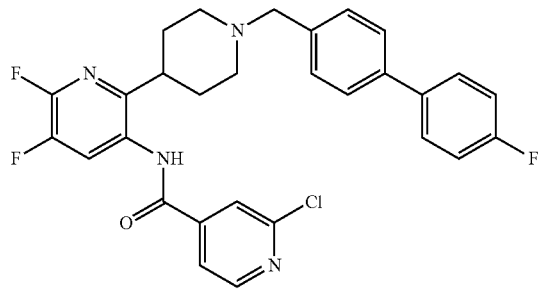 [SMILES: O=C(Nc1cc(F)c(F)nc1C1CCN(Cc2ccc(-c3ccc(F)cc3)cc2)CC1)c1ccnc(Cl)c1]

Step A: To a solution of the compound obtained in Step C of Example 4 (5 g) and trifluoroacetic acid (46.5 ml) in chloroform (324 ml) at 50° C. was added dropwise aqueous hydrogen peroxide (30% by weight) (15.7 ml). The reaction mixture was stirred at 55° C. for 1 hour, cooled to ambient temperature and diluted with dichloromethane. The solution was washed with water and brine, dried over sodium sulfate and concentrated in vacuo to afford the intermediate, 6-chloro-5-fluoro-3-nitro-1',2',3',4',5',6'-hexahydro-[2,4]bipyridinyl (4 g), as an oil. MS (ES+) 260 (MH+). The intermediate was treated with di-tert-butyl-dicarbonate (4 g) and triethylamine (6.3 ml) in dichloromethane (250 ml) for 12 hours to afford, after aqueous work-up, 6-chloro-5-fluoro-3-nitro-3',4',5',6'-tetrahydro-2'H-[2,4]bipyridinyl-1'-carboxylic acid tent-butyl ester (4.3 g) as a red oil. MS (ES+) 360 (MH+), 345 (M-isoprene+CH$_3$CN), 305 (M-isoprene), 260 (MH+-BOC).

Step B: The product obtained in Step A (3.3 g), spray dried potassium fluoride (1.06 g) and tetraphenylphosphonium bromide (7.6 g) were dissolved in acetonitrile (23 ml) and the reaction mixture was heated to reflux for 8 hours. The reaction mixture was cooled to ambient temperature, the white solid removed by filtration and the filtrate concentrated in vacuo. Chromatography on silica gel (eluent: cyclohexane/ethyl acetate 9:1) afforded 5,6-difluoro-3-nitro-3',4',5',6'-tetrahydro-2'H-[2,4]bipyridinyl-1'-carboxylic acid tert-butyl ester (0.85 g): MS (ES+) 329 (M-isoprene+CH$_3$CN), 288 (M-isoprene), 244 (MH+-BOC); 1H NMR (400 MHz, CDCl$_3$) 1.45 (s, 9H), 1.80 (m, 4H), 2.79 (m, 1H), 3.43 (m, 2H), 4.22 (m, 2H), 8.13 (t, 1H).

Step C: The product obtained in Step B (694 mg) was hydrogenated at ambient temperature in methanol to afford 3-amino-5,6-difluoro-3',4',5',6'-tetrahydro-2'H-[2,4]bipyridinyl-1'-carboxylic acid tert-butyl ester (390 mg) as a yellow oil: MS (ES+) 314 (MH+), 258 (M-isoprene); 1H NMR (400 MHz, CDCl$_3$) 1.45 (s, 9H), 1.75 (m, 4H), 2.70 (m, 1H), 2.80 (m, 2H), 3.90 (m, 2H), 4.23 (m, 2H), 6.90 (t, 1H).

The product obtained in Step C (313 mg) was converted into the title product following procedures analogous to those described in Example 4 (Step D and Step E).

EXAMPLE 13

This example illustrates the preparation of 2-chloro-N-{1'-(4'-fluoro-biphenyl-4-ylmethyl)-6-difluoromethyl-1',2',3',4',5',6'-hexahydro-[2,4]bipyridinyl-3-yl}-isonicotinamide (Compound C6 of Table C).

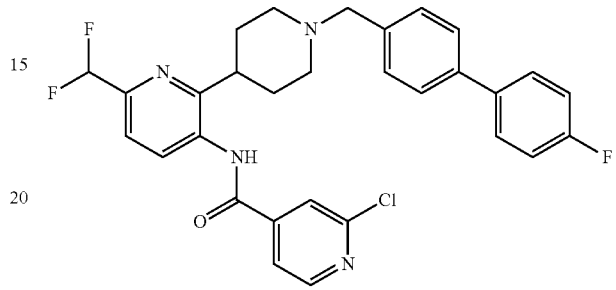

Step A: 6-(Chlorodifluoromethyl)-nicotinonitrile (35.4 g, prepared as described in Tetrahedron Letters, 39 (43), 1998, 7965) was suspended in concentrated hydrochloric acid (245 ml) and stirred at 110° C. for 16 hours. The reaction mixture was cooled to ambient temperature and a mixture of ice and water was added. The white solid was isolated by filtration and dried in high vacuum to give 6-(chlorodifluoromethyl)-nicotinic acid (36 g). 1H NMR (400 MHz, DMSOd$_6$) 3.30 (br s, 1H), 8.00 (dd, 1H), 8.51 (dd, 1H), 9.17 (d, 1H).

Step B: Under a nitrogen atmosphere, a solution of tent-butanol (100 ml), molecular sieve powder (4 angstrom) (23 g) and triethylamine was prepared (9.36 ml). After stirring for 5 minutes at ambient temperature, the compound obtained in Step A (10 g) was added, followed by diphenyl phosphoryl azide (16.3 g). The reaction mixture was heated to reflux for 3 hours and then filtered through Celite®. The reaction mixture was poured into water and extracted several times with diethyl ether. The combined organic layers were washed with brine, dried over sodium sulfate and then concentrated in vacuo. Chromatography on silica gel (eluent: hexane/ethyl acetate 5:1) afforded [6-(chlorodifluoromethyl)-pyridin-3-yl]-carbamic acid tert-butyl ester (10.6 g). MS (ES+) 279/281 (MH+); 1H NMR (400 MHz, CDCl$_3$) 1.55 (s, 9H), 7.52 (d, 1H), 8.19 (m, 1H), 8.47 (d, 1H).

Step C: The compound obtained in Step B (5.57 g) was dissolved in ethanol (110 ml) and after degassing, palladium on charcoal (10% by weight) (1 g) was added. Under a hydrogen atmosphere, the reaction mixture was stirred at ambient temperature for 5 hours. Filtration on Celite® furnished (6-difluoromethyl-pyridin-3-yl)-carbamic acid tert-butyl ester (4.8 g) as a foam. MS (ES+) 245/246 (MH+); 1H NMR (400 MHz, CDCl$_3$) 1.54 (s, 9H), 7.15 (t, 1H), 7.91 (m, 1H), 9.03 (m, 1H), 9.33 (m, 2H).

Step D: A solution of the compound obtained in Step C (5.9 g) in dichloromethane (80 ml) was treated with trifluoroacetic acid (3.7 ml) at ambient temperature for 12 hours. The reaction mixture was poured into aqueous sodium hydrogen carbonate (saturated) and washed several times with dichloromethane. The combined organic layers were washed with brine, dried over sodium sulfate and then concentrated in vacuo. Chromatography on silica gel (eluent: hexane/ethyl acetate 1:1) afforded 6-difluoromethyl-pyridin-3-yl-amine (2.1 g): 1H NMR (400 MHz, CDCl$_3$) 3.98 (br s, 2H), 6.56 (t, 1H), 7.03 (dd, 1H), 7.40 (d, 1H), 8.06 (d, 1H).

Step E: A solution of the compound obtained in Step D (2.1 g) and N-bromo-succinimide (2.56 g) in acetonitrile (50 ml) was stirred at 0° C. for 10 minutes. The reaction mixture was poured into water and extracted several times with ethyl acetate. The combined organic layers were washed with brine, dried over sodium sulfate and then concentrated in vacuo. Chromatography on silica gel (eluent: hexane/ethyl acetate 1:1) afforded 2-bromo-6-difluoromethyl-pyridin-3-yl-amine (2.5 g) as a solid. MS (ES+) 223/225 (MH+); 1H NMR (400 MHz, CDCl$_3$) 4.38 (br s, 2H), 6.52 (t, 1H), 7.08 (d, 1H), 7.41 (d, 1H).

The compound obtained in Step E was then treated according to the procedures described in Example 4 (Step A, Step B, Step C and Step D) to obtain the title compound.

EXAMPLE 14

This example illustrates the preparation of 2-chloro-N-{1'-(4'-fluoro-biphenyl-4-ylmethyl)-6-difluoromethoxy-1',2',3',4',5',6'-hexahydro-[2,4']bipyridinyl-3-yl}-isonicotinamide (Compound C40 of Table C).

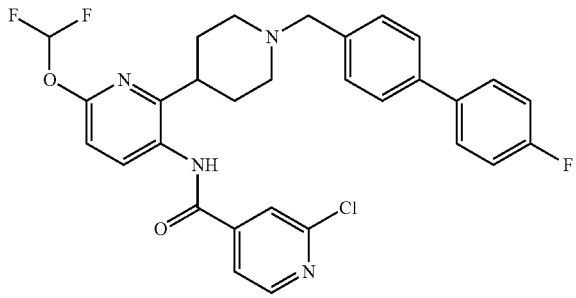 [SMILES: O=C(Nc1ccc(OC(F)F)nc1C1CCN(Cc2ccc(-c3ccc(F)cc3)cc2)CC1)c1ccnc(Cl)c1]

The title compound was obtained from 2-bromo-6-difluoromethoxy-pyridin-3-yl-amine following the procedures described in Example 4. 2-Bromo-6-difluoromethoxy-pyridin-3-yl-amine was prepared as follows:

Step A: 2-Hydroxy-5-nitro-pyridine (5 g) was treated with sodium chlorodifluoro-acetate (11.5 g) in refluxing acetonitrile (186 ml) for 2 days. The solvent was evaporated, the residue poured into ethyl acetate, washed with brine, dried over sodium sulfate and then concentrated in vacuo. Chromatography on silica gel (eluent: hexane/ethyl acetate 1:1) afforded 2-difluoromethoxy-5-nitro-pyridine (1 g, 15%) and 1-difluoromethyl-5-nitro-1H-pyridin-2-one (90 mg, 1.5%). 2-Difluoromethoxy-5-nitro-pyridine: MS (ES+) 191 (MH+); 1H NMR (400 MHz, CDCl$_3$) 7.05 (d, 1H), 7.51 (t, 1H), 8.53 (dd, 1H), 9.09 (d, 1H). 1-Difluoromethyl-5-nitro-1H-pyridin-2-one: MS (ES+) 191 (MH+); 6.65 (d, 1H), 7.63 (t, 1H), 8.14 (dd, 1H), 8.73 (d, 1H).

Step B: 2-Difluoromethoxy-5-nitro-pyridine obtained in Step A (1.6 g) was treated with iron (5 g) and concentrated hydrochloric acid (0.23 ml) in ethanol (15 ml) and water (2.5 ml) at 80° C. for 20 minutes. Filtration over Celite® and evaporation of the solvent afforded 6-difluoromethoxy-pyridin-3-yl-amine (1.4 g) as an orange solid. 1H NMR (400 MHz, CDCl$_3$) 3.51 (br s, 2H), 6.89 (d, 1H), 7.23 (d, 1H), 7.44 (dd, 1H), 7.80 (d, 1H).

Step C: 6-Difluoromethoxy-pyridin-3-yl-amine obtained in Step B (1.36 g) was treated with N-bromosuccinimide (1.51 g) in acetonitrile for 10 minutes. The solution was poured into water, extracted with ethyl acetate, the organic layer dried over sodium sulfate and concentrated in vacuo. Chromatography on silica gel (eluent: cyclohexane/ethyl acetate 7:3) afforded 2-bromo-6-difluoromethoxy-pyridin-3-yl-amine as a red oil. 1H NMR (400 MHz, CDCl$_3$) 3.95 (br s, 2H), 6.72 (d, 1H), 7.07 (d, 1H), 7.24 (dd, 1H).

EXAMPLE 15

This example illustrates the preparation of 2-chloro-N-[5-chloro-1'-(4'-fluoro-biphenyl-4-ylmethyl)-6-(2,2,2-trifluoro-ethoxy)-1',2',3',4',5',6'-hexahydro-[2,4']bipyridinyl-3-yl]-isonicotinamide (Compound C9 of Table C).

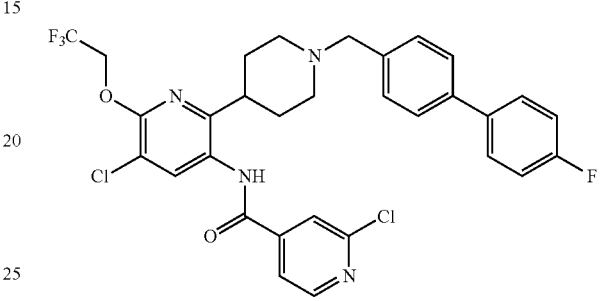

The title compound was obtained from 2-bromo-5-chloro-6-trifluoroethoxy-pyridin-3-yl-amine following the procedures described in Example 5 (without Step C). 2-Bromo-5-chloro-6-trifluoroethoxy-pyridin-3-yl-amine was prepared as follows:

Step A: A solution of 2,3-dichloro-5-nitro-pyridine (5 g, *Synthesis*, 1990 (6), 499-501), 2,2,2-trifluoroethanol (2.6 g) and potassium carbonate (5.4 g) in N,N-dimethylformamide (50 ml) was stirred at 80° C. for 1 hour. The reaction mixture was poured into ice water. The precipitate was isolated by filtration and dried under high vacuum to afford 3-chloro-5-nitro-2-(2,2,2-trifluoro-ethoxy)-pyridine (5.65 g).

Step B: 3-Chloro-5-nitro-2-(2,2,2-trifluoroethoxy)-pyridine (5.39 g) obtained in Step A was reduced with iron (13.6 g) and concentrated hydrochloric acid (0.73 ml) in ethanol (6.5 ml) and water (1 ml) at 80° C. for 1 hour. Filtration over Celite® and evaporation of the solvent followed by chromatography on silica gel (eluent: cyclohexane/ethyl acetate 9:1) afforded 3-chloro-5-amino-2-(2,2,2-trifluoro-ethoxy)-pyridine (3.1 g).

Step C: 3-Chloro-5-amino-2-(2,2,2-trifluoroethoxy)-pyridine (3.05 g) obtained in Step B was brominated with N-bromosuccinimide (2.4 g) in acetonitrile (68 ml) as described in Example 14, Step C to give 2-bromo-5-chloro-6-trifluoroethoxy-pyridin-3-yl-amine (4.12 g) as a red oil. MS (ES+) 305/307/309 (MH+); 346/348/350 (MH$^+$+CH$_3$CN); 1H NMR (400 MHz, CDCl$_3$) 3.80 (br s, 2H), 4.65 (q, 2H), 7.10 (s, 1H).

EXAMPLE 16

This example illustrates the preparation of 2-chloro-N-[1'-(4'-fluoro-biphenyl-4-ylmethyl)-6-methoxy-1',2',3',4',5',6'-hexahydro-[2,4']bipyridinyl-3-yl]-isonicotinamide (Compound C10 of Table C).

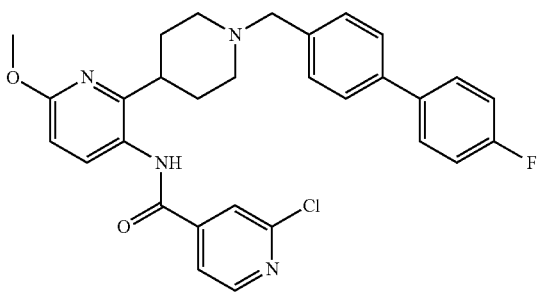 [SMILES: COc1ccc(NC(=O)c2ccnc(Cl)c2)c(C2CCN(Cc3ccc(-c4ccc(F)cc4)cc3)CC2)n1]

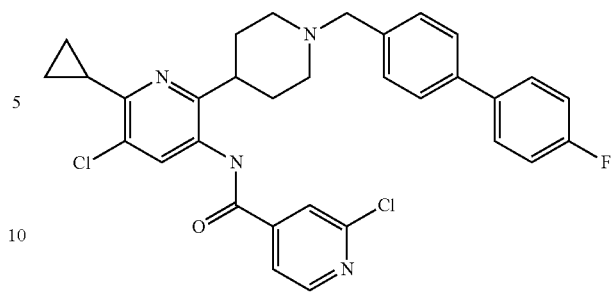

The title compound was obtained from 2-chloro-6-methoxy-pyridin-3-yl-amine following the procedures described in Example 3.

EXAMPLE 17

This example illustrates the preparation of 2-chloro-N-[1'-(4'-fluoro-biphenyl-4-ylmethyl)-6-vinyl-1',2',3',4',5',6'-hexahydro-[2,4]bipyridinyl-3-yl]-isonicotinamide (Compound C11 of Table C).

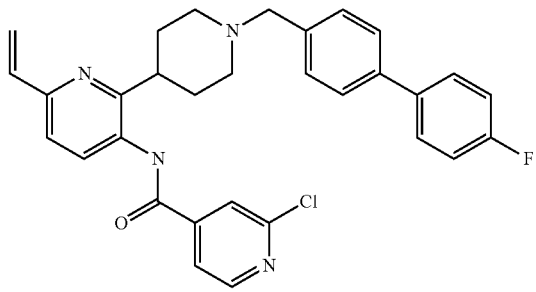 [SMILES: C=Cc1ccc(NC(=O)c2ccnc(Cl)c2)c(C2CCN(Cc3ccc(-c4ccc(F)cc4)cc3)CC2)n1]

The title compound was obtained from 3-amino-6-vinyl-3',4',5',6'-tetrahydro-2'H-[2,4]bipyridinyl-1'-carboxylic acid tert-butyl ester following the procedures described in Example 3, Step C to Step E. 3-Amino-6-vinyl-3',4',5',6'-tetrahydro-2'H-[2,4]bipyridinyl-1'-carboxylic acid tert-butyl ester was obtained as follows:

A solution of 3-amino-6-bromo-3',4',5',6'-tetrahydro-2'H-[2,4]bipyridinyl-1'-carboxylic acid tert-butyl ester (0.49 g, prepared from 3-amino-2-bromo-pyridine following procedures described in Example 6, Step A to Step C), tributylvinyl tin (0.36 g), tetrakis(triphenylphosphine)palladium (0.035 g) in toluene (20 ml) was heated at reflux for 3 hours. The reaction mixture was cooled to ambient temperature and the solvent removed in vacuo. The residue was purified by chromatography on silica gel (eluent: cyclohexane/ethyl acetate 1:1) to afford 3-amino-6-vinyl-3',4',5',6'-tetrahydro-2'H-[2,4]bipyridinyl-1'-carboxylic acid tert-butyl ester (0.32 g) as a yellow solid. MS (ES+) 443/445 (MH+); 1H NMR (400 MHz, CDCl$_3$) 1.40 (s, 9H), 1.70 (m, 2H), 1.90 (m, 2H), 2.75 (m, 2H), 2.80 (m, 1H), 4.15 (m, 2H), 5.4 (d, 1H), 6.2 (d, 1H), 6.7 (dd, 1H), 7.15 (d, 1H), 7.6 (d, 1H), 7.7 (s, 1H), 7.8 (m, 1H), 7.9 (s, 1H), 8.5 (d, 1H).

EXAMPLE 18

This example illustrates the preparation of 2-chloro-N-[5-chloro-6-cyclopropyl-1'-(4'-fluoro-biphenyl-4-ylmethyl)-1',2',3',4',5',6'-hexahydro-[2,4]bipyridinyl-3-yl]-isonicotinamide (Compound C13 of Table C).

The title compound was obtained from 3-amino-5-chloro-6-cyclopropyl-3',4',5',6'-tetrahydro-2'H-[2,4]bipyridinyl-1'-carboxylic acid tert-butyl ester following the procedures described in Example 3, Step C to Step E. 3-Amino-5-chloro-6-cyclopropyl-3',4',5',6'-tetrahydro-2'H-[2,4]bipyridinyl-1'-carboxylic acid tert-butyl ester was obtained as follows:

A solution of 3-amino-5-chloro-6-bromo-3',4',5',6'-tetrahydro-2'H-[2,4]bipyridinyl-1'-carboxylic acid tert-butyl ester (0.59 g, prepared following procedures described in Example 5 with N-bromosuccinimide instead of N-chlorosuccinimide in Step C), cyclopropyl boronic acid (0.086 g), tetrakis(triphenylphosphine)palladium (0.094 g), potassium carbonate (0.14 g) in 1,2-dimethoxyethane (5 ml) and water (0.2 ml) was irradiated in a microwave at 150° C. for 20 minutes. The reaction mixture was cooled to ambient temperature, diluted with ethyl acetate, washed with aqueous sodium hydrogen carbonate (saturated), water then brine. The organic layer was dried over sodium sulfate and the solvent removed in vacuo. The residue was purified by chromatography on silica gel (eluent: dichloromethane/ethyl acetate 9:1) to afford 3-amino-5-chloro-6-cyclopropyl-3',4',5',6'-tetrahydro-2'H-[2,4]bipyridinyl-1'-carboxylic acid tert-butyl ester (0.30 g) as a yellow solid. MS (ES+) 491/493 (MH+); 1H NMR (400 MHz, CDCl$_3$) 1.0-1.1 (m, 4H), 1.45 (s, 9H), 1.60 (m, 1H), 1.70 (m, 2H), 1.85 (m, 2H), 2.50 (m, 1H), 2.80 (m, 2H), 4.20 (m, 2H), 7.65 (d, 1H), 7.75 (s, 1H), 7.80 (s, 1H), 7.9 (m, 1H), 8.60 (d, 1H).

EXAMPLE 19

This example illustrates the preparation of N-[5-bromo-1'-(4'-fluoro-biphenyl-4-ylmethyl)-1',2',3',4',5',6'-hexahydro-[2,4]bipyridinyl-3-yl]-2-chloro-isonicotinamide (Compound C23 of Table C).

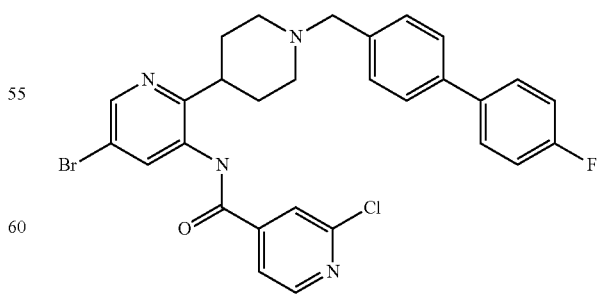

The title compound was obtained from 2,5-dibromo-3-aminopyridine following the procedures described in Example 5, without Step C.

EXAMPLE 20

This example illustrates the preparation of N-[5-bromo-6-chloro-1'-(4'-fluoro-biphenyl-4-ylmethyl)-1',2',3',4',5',6'-hexahydro-[2,4]bipyridinyl-3-yl]-2-chloro-isonicotinamide (Compound C24 of Table C).

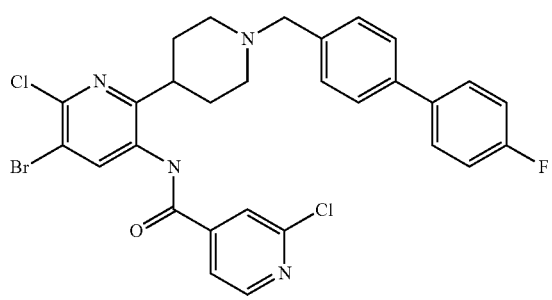

The title compound was obtained from 2,5-dibromo-3-aminopyridine following the procedures described in Example 5.

EXAMPLE 21

This example illustrates the preparation of 2-chloro-N-[6-chloro-1'-(4'-fluoro-biphenyl-4-ylmethyl)-5-methyl-1',2',3',4',5',6'-hexahydro-[2,4]bipyridinyl-3-yl]-isonicotinamide (Compound C26 of Table C).

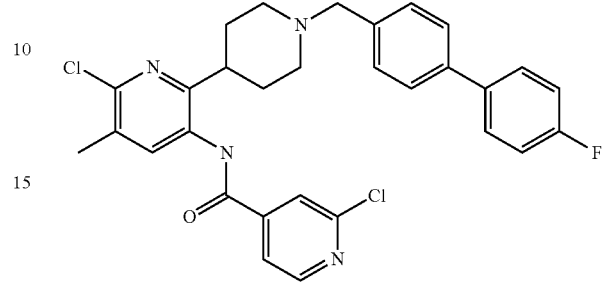

The title compound was obtained from 2-bromo-5-methyl-3-aminopyridine following the procedures described in Example 4.

The following compounds were prepared according to procedures analogous to those described in Examples 3 to 21:

TABLE C

Compounds of formula (Ic)

| Comp No | $R^1$ | $R^3$ | $R^4$ | $R^5$ | $R^8$ | Physical state/ M.p. | HPLC (RT) | MS (ES+) |
|---|---|---|---|---|---|---|---|---|
| C1 | 2-chloro-pyrid-4-yl | —CF$_3$ | H | H | F | 63-66° C. | 1.42 min | 569/571 |
| C2 | 2-chloro-pyrid-4-yl | Cl | Cl | H | F | 84-86° C. | 1.46 min | 569/571 |
| C3 | 2-fluoro-pyrid-4-yl | —CF$_3$ | H | H | F | solid | 1.40 min | 553 |
| C4 | 2,6-dichloro-pyrid-4-yl | —CF$_3$ | H | H | F | solid | 1.51 min | 603/605/607 |
| C5 | 2-chloro-pyrid-4-yl | Br | F | H | F | 88-93° C. | 1.41 min | 597/599 |
| C6 | 2-chloro-pyrid-4-yl | —CHF$_2$ | H | H | F | solid | 1.36 min | 551/553 |
| C7 | 2-(chloro-difluoro-methyl)-pyrid-4-yl | —CF$_3$ | H | H | F | solid | 1.48 min | 619/621/623 |
| C8 | 2,6-dichloro-pyrid-4-yl | —CHF$_2$ | H | H | F | solid | 1.45 min | 585/587/589 |

TABLE C-continued

Compounds of formula (Ic)

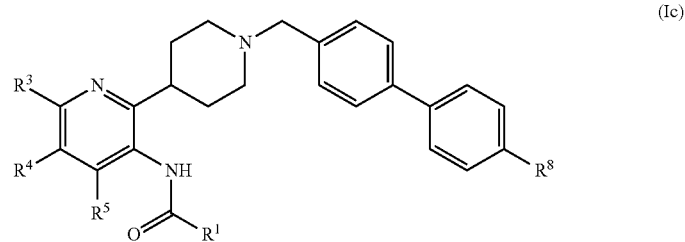

(Ic)

| Comp No | R¹ | R³ | R⁴ | R⁵ | R⁸ | Physical state/ M.p. | HPLC (RT) | MS (ES+) |
|---|---|---|---|---|---|---|---|---|
| C9 | 2-chloro-pyrid-4-yl | —OCH₂CF₃ | Cl | H | F | 82-86° C. | 1.52 min | 633/635 |
| C10 | 2-chloro-pyrid-4-yl | —OCH₃ | H | H | F | 87-90° C. | 1.35 min | 531 |
| C11 | 2-chloro-pyrid-4-yl | —CH═CH₂ | H | H | F | 79-80° C. | 1.36 min | 527 |
| C12 | 2-chloro-pyrid-4-yl | —CH═CH₂ | Cl | H | F | 88-90° C. | 1.60 min | 561/563 |
| C13 | 2-chloro-pyrid-4-yl | cyclo-propyl | Cl | H | F | 78-80° C. | 1.63 min | 575/577 |
| C14 | 2-chloro-pyrid-4-yl | cyclo-propyl | H | H | F | solid | 1.52 min | 541/543 |
| C15 | 2-chloro-pyrid-4-yl | Br | —CF₃ | H | F | solid | 1.63 min | 649/651/653 |
| C16 | 2-chloro-pyrid-4-yl | Cl | —CF₃ | H | F | solid | 1.49 min | 603/605/607 |
| C17 | 2-chloro-pyrid-4-yl | Cl | F | H | F | 84-93° C. | 1.39 min | 553/555 |
| C18 | 2,5-dichloro-pyrid-4-yl | —CF₃ | H | H | F | solid | 1.47 min | 603/605/607 |
| C19 | 2-fluoro-pyrid-4-yl | Cl | Cl | H | F | 91-95° C. | 1.40 min | 553/555 |
| C20 | 2-chloro-6-methyl-pyrid-4-yl | Cl | Cl | H | F | 94-98° C. | 1.47 min | 583/585 |
| C21 | 2-chloro-pyrid-4-yl | cyclo-propyl | F | H | F | 82-83° C. | 1.48 min | 559/561 |
| C22 | 2-chloro-pyrid-4-yl | H | cyclo-propyl | H | F | 118-120° C. | 1.37 min | 541/543 |
| C23 | 2-chloro-pyrid-4-yl | H | Br | H | F | 87-89° C. | 1.39 min | 579/581 |
| C24 | 2-chloro-pyrid-4-yl | Cl | Br | H | F | 88-89° C. | 1.47 min | 615/617 |
| C25 | 2-chloro-pyrid-4-yl | F | F | H | F | 71-73° C. | 1.38 min | 537/539 |
| C26 | 2-chloro-pyrid-4-yl | Cl | —CH₃ | H | F | foam | 1.40 min | 549/551 |
| C27 | 2-chloro-pyrid-4-yl | —CF₃ | H | H | H | — | 1.29 min. | 551.2 |

TABLE C-continued

Compounds of formula (Ic)

(Ic)

| Comp No | R¹ | R³ | R⁴ | R⁵ | R⁸ | Physical state/ M.p. | HPLC (RT) | MS (ES+) |
|---|---|---|---|---|---|---|---|---|
| C28 | 2-chloro-pyrid-4-yl | —CF₃ | H | H | Cl | 70° C. | 1.55 min | 585/587 |
| C29 | 2-chloro-pyrid-4-yl | —CF₃ | H | H | —CH₃ | — | 1.32 min. | 565.2 |
| C30 | 2-chloro-pyrid-4-yl | Cl | Cl | Cl | F | 101-105° C. | 1.49 min | 605/607 |
| C31 | 2-chloro-pyrid-4-yl | F | —CF₃ | H | F | foam | 1.45 min | 585/587 |
| C32 | 2-chloro-pyrid-4-yl | Cl | Cl | H | Cl | 131-136° C. | 1.48 min | 587/589 |
| C33 | 2-chloro-pyrid-4-yl | —CF₃ | H | H | —CF₃ | 131-133° C. | 1.53 min | 619/621 |
| C34 | 2-chloro-pyrid-4-yl | Cl | Cl | H | —CF₃ | 135-140° C. | 1.52 min | 621/623 |
| C35 | 2-chloro-pyrid-4-yl | —CF₃ | H | H | —OCH₃ | 75-80° C. | 1.41 min | 581/583 |
| C36 | 2-trifluoromethyl-pyrid-4-yl | —CF₃ | H | H | F | foam | 1.50 min | 603/604 |
| C37 | 2,5-dichloro-pyrid-4-yl | Cl | Cl | H | F | 66-68° C. | 1.53 min | 604/606 |
| C38 | 5-chloro-2-fluoro-pyrid-4-yl | —CF₃ | H | H | F | foam | 1.43 min | 587/589 |
| C39 | 2-chloro-5-fluoro-pyrid-4-yl | —CF₃ | H | H | F | foam | 1.44 min | 587/589 |
| C40 | 2-chloro-pyrid-4-yl | —OCHF₂ | H | H | F | 82-83° C. | 1.49 min | 567/569 |
| C41 | 2-chloro-pyrid-4-yl | —CF₃ | H | F | F | foam | 1.45 min | 587/589 |
| C42 | 2-chloro-pyrid-4-yl | —CF₃ | H | H | —CN | 96° C. | 1.39 min | 576/578 |
| C43 | 2-chloro-pyrid-4-yl | —CF₃ | H | H | —OCF₃ | 63-64° C. | 1.56 min | 635/637 |
| C44 | 2-chloro-pyrid-4-yl | —CF₃ | H | H | Br | 69-70° C. | 1.52 min | 629/631 |
| C45 | 2-chloro-pyrid-4-yl | —CF₃ | H | H | -cyclopropyl | 86-87° C. | 1.54 min | 591/593 |

TABLE C-continued

Compounds of formula (Ic)

![Structure Ic]

| Comp No | R¹ | R³ | R⁴ | R⁵ | R⁸ | Physical state/ M.p. | HPLC (RT) | MS (ES+) |
|---|---|---|---|---|---|---|---|---|
| C46 | 2-chloro-pyrid-4-yl | —CF₃ | H | H | —C≡CH | | 1.48 min | 575 |
| C47 | 3-trifluoro-methyl-pyrid-4-yl | —CF₃ | H | H | F | | 1.30 min | 603 |
| C48 | pyrid-4-yl | —CF₃ | H | H | F | | 1.08 min | 535 |
| C49 | 2-chloro-6-propyl-pyrid-4-yl | —CF₃ | H | H | F | | 1.47 min | 611 |
| C50 | 2-chloro-6-ethyl-pyrid-4-yl | —CF₃ | H | H | F | | 1.39 min | 597 |
| C51 | 2,5-difluoro-pyrid-4-yl | —CF₃ | H | H | F | | 1.34 min | 507/509 |

EXAMPLE 22

This example illustrates the preparation of 2-chloro-N-[1'-(4'-fluoro-biphenyl-4-ylmethyl)-1'-oxy-6-trifluoromethyl-1',2',3',4',5',6'-hexahydro-[2,4]bipyridinyl-3-yl]-isonicotinamide (Compound D1 of Table D).

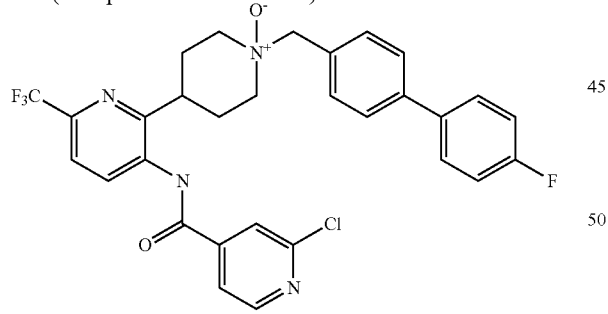

To a solution of 2-chloro-N-[1'-(4'-fluoro-biphenyl-4-ylmethyl)-6-trifluoromethyl-1',2',3',4',5',6'-hexahydro-[2,4]bipyridinyl-3-yl]-isonicotinamide (2.4 g) (Example 3) in methanol (10 ml) was added aqueous hydrogen peroxide (30% by weight) (2.9 g) at ambient temperature. The reaction mixture was stirred at 55° C. for 16 hours. The solution was concentrated to one third of its volume and the precipitate isolated by filtration and dried under high vacuum to afford the title compound as a white powder (1.5 g). M.p. 158-161° C.; MS (ES+) 585/587 (MH+); 1H NMR (400 MHz, CDCl₃) 1.83 (m, 2H), 2.71 (m, 2H), 3.27-3.46 (m, 5H), 4.48 (s, 2H), 7.15 (m, 2H), 7.45-7.60 (m, 8H), 7.91 (dd, 1H), 8.02 (d, 1H), 8.05 (bs, 1H), 8.54 (d, 1H).

The following compounds were prepared according to procedures analogous to the procedure described in Example 22:

TABLE D

Compounds of formula (Id)

(Id)

| Comp No | R¹ | R³ | R⁴ | R⁵ | R⁸ | Physical state/ M.p. | HPLC (RT) | MS (ES+) |
|---|---|---|---|---|---|---|---|---|
| D1 | 2-chloro-pyrid-4-yl | —CF₃ | H | H | F | 158-161° C. | 1.44 min | 585/587 |
| D2 | 2-chloro-pyrid-4-yl | Cl | Cl | H | F | 198-203° C. | 1.48 min | 585/587 |
| D3 | 2-fluoro-pyrid-4-yl | —CF₃ | H | H | F | 198-200° C. | 1.45 min | 569/571 |
| D4 | 2,6-dichloro-pyrid-4-yl | —CF₃ | H | H | F | 197-198° C. | 1.54 min | 619/621/623 |
| D5 | 2-chloro-pyrid-4-yl | —OCH₂CF₃ | Cl | H | F | 202-206° C. | 1.45 min | 649/651 |
| D6 | 2-chloro-pyrid-4-yl | Br | —CF₃ | H | F | 190-191° C. | 1.61 min | 665/667/669 |
| D7 | 2-chloro-pyrid-4-yl | Br | F | H | F | 174-177° C. | 1.47 min | 613/615 |
| D8 | 2-chloro-pyrid-4-yl | Cl | F | H | F | 174-178° C. | 1.44 min | 569/571 |
| D9 | 2,5-dichloro-pyrid-4-yl | —CF₃ | H | H | F | 164-168° C. | 1.52 min | 619/621/623 |
| D10 | 2-fluoro-pyrid-4-yl | Cl | Cl | H | F | 177-181° C. | 1.47 min | 569/571 |
| D11 | 2-chloro-6-methyl-pyrid-4-yl | Cl | Cl | H | F | 168-174° C. | 1.52 min | 599/601 |
| D12 | 2-chloro-pyrid-4-yl | Cl | —CF₃ | H | F | 208-210° C. | 1.53 min | 619/621/623 |
| D13 | 2-chloro-pyrid-4-yl | cyclo-propyl | H | H | F | 180-182° C. | 1.44 min | 557/559 |
| D14 | 2-chloro-pyrid-4-yl | cyclo-propyl | Cl | H | F | 172-175° C. | 1.54 min | 591/593 |
| D15 | 2-chloro-pyrid-4-yl | —OCH₃ | H | H | F | 213-219° C. | 1.43 min | 547/549 |
| D16 | 2-chloro-pyrid-4-yl | Cl | Br | H | F | 185° C. | 1.49 min | 631/633 |
| D17 | 2-chloro-pyrid-4-yl | Cl | —CH₃ | H | F | foam | 1.43 min | 565/567 |
| D18 | 2-chloro-pyrid-4-yl | Cl | Cl | Cl | F | 188-191° C. | 1.53 min | 621/623 |

TABLE D-continued

Compounds of formula (Id)

(Id)

| Comp No | R¹ | R³ | R⁴ | R⁵ | R⁸ | Physical state/ M.p. | HPLC (RT) | MS (ES+) |
|---|---|---|---|---|---|---|---|---|
| D19 | 2-chloro-pyrid-4-yl | F | —CF₃ | H | F | foam | 1.48 min | 603/605 |
| D20 | 2-chloro-pyrid-4-yl | Cl | Cl | H | —CF₃ | 148-151° C. | 1.61 min | 637/639 |
| D21 | 2-chloro-pyrid-4-yl | —CF₃ | H | H | Cl | 183-186° C. | 1.53 min | 601/603 |
| D22 | 2-trifluoromethyl-pyrid-4-yl | —CF₃ | H | H | F | foam | 1.52 min | 619/620 |
| D23 | 2-chloro-pyrid-4-yl | —CF₃ | H | H | —OCH₃ | 180-182° C. | 1.42 min | 597/599 |
| D24 | 5-chloro-2-fluoro-pyrid-4-yl | —CF₃ | H | H | F | 178-180° C. | 1.46 min | 603/605 |
| D25 | 2-chloro-5-fluoro-pyrid-4-yl | —CF₃ | H | H | F | 173-175° C. | 1.48 min | 603/605 |
| D26 | 2-chloro-pyrid-4-yl | —OCHF₂ | H | H | F | 203° C. | 1.43 min | 583/585 |
| D27 | 2-chloro-pyrid-4-yl | —CF₃ | H | F | F | foam | 1.47 min | 603/605 |

EXAMPLE 23

This example illustrates the preparation of 2-chloro-N-{3,4,5-trifluoro-2-[1-(4'-fluoro-biphenyl-4-ylmethyl)-piperidin-4-yl]-phenyl}-isonicotinamide (Compound E1 of Table E).

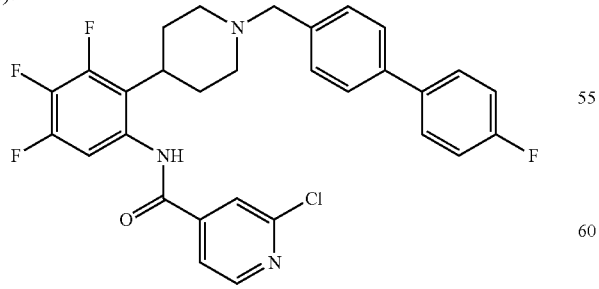

The title compound was prepared from 2-bromo-3,4,5-trifluoroaniline according to the method described in Example 4.

The following compounds were prepared according to procedures analogous to the procedure described in Example 23:

TABLE E

Compounds of formula (Ie)

| Comp No | R¹ | R³ | R⁴ | R⁵ | R⁸ | Physical state/ M.p. | HPLC (RT) | MS (ES+) |
|---|---|---|---|---|---|---|---|---|
| E1 | 2-chloro-pyrid-4-yl | F | F | H | F | 61-64° C. | 1.43 min | 554/556 |
| E2 | 2-chloro-pyrid-4-yl | —CF₃ | F | H | F | 65-69° C. | 1.54 min | 604/606 |
| E3 | 2-chloro-pyrid-4-yl | Cl | H | H | F | 105-109° C. | 1.39 min | 552/554/556 |
| E4 | 2-chloro-pyrid-4-yl | H | H | H | F | 164-167° C. | 1.41 min | 518/520 |
| E5 | 2-chloro-pyrid-4-yl | Br | H | H | F | 194-198° C. | 1.39 min | 596/598/600 |
| E6 | 2-chloro-pyrid-4-yl | —CN | H | H | F | 125-129° C. | 1.37 min | 543/545 |
| E7 | 2-chloro-pyrid-4-yl | F | H | H | F | 92-95° C. | 1.36 min | 536/538 |
| E8 | 2-chloro-pyrid-4-yl | —CF₃ | H | H | F | 93-96° C. | 1.44 min | 586/588 |
| E9 | 2-chloro-pyrid-4-yl | cyclopropyl | H | H | F | 124-128° C. | 1.44 min | 558/560 |

EXAMPLE 24

This example illustrates the preparation of 2-chloro-N-{3-trifluoromethyl-2-[1-(4'-chloro-biphenyl-4-ylmethyl)-piperidin-4-yl]-phenyl}-isonicotinamide (Compound F1 of Table F).

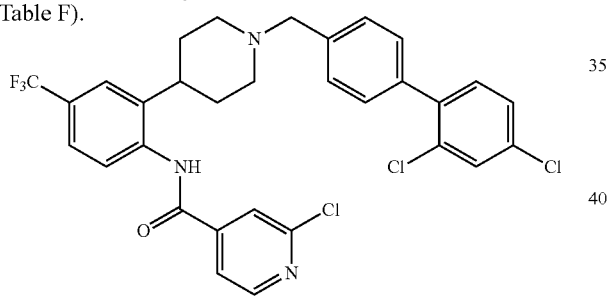

The title compound was obtained according to the method described in Example 3 using 2',4'-dichloro-biphenyl-4-carbaldehyde instead of 4'-fluoro[1,1'-biphenyl]-4-carboxaldehyde (Step E, Method B). 2',4'-Dichloro-biphenyl-4-carbaldehyde was prepared by Suzuki coupling between 1-bromo-2,4-dichlorobenzene and 4-formylbenzeneboronic acid.

The following compounds were prepared according to procedures analogous to the procedure described in Example 24:

TABLE F

Compounds of formula (If)

| Comp No | A | R¹ | R³ | R⁴ | R⁶ | R⁷ | R⁸ | Physical state/ M.p. | HPLC (RT) | MS (ES+) |
|---|---|---|---|---|---|---|---|---|---|---|
| F1 | CH | 2-chloro- | —CF₃ | H | — | 1'-Cl | Cl | 129-133° C. | 1.56 min | 620/622 |

TABLE F-continued

Compounds of formula (If)

(If)

| Comp No | A | R¹ | R³ | R⁴ | R⁶ | R⁷ | R⁸ | Physical state/ M.p. | HPLC (RT) | MS (ES+) |
|---|---|---|---|---|---|---|---|---|---|---|
| F2 | CH | 2-chloro-pyrid-4-yl | —CF₃ | H | — | 1'-F | F | 152-156° C. | 1.46 min | 586/588 |
| F3 | CH | 2-chloro-pyrid-4-yl | —CF₃ | H | — | 1'-Me | F | 68-72° C. | 1.49 min | 582/584 |
| F4 | CH | 2-chloro-pyrid-4-yl | —CF₃ | H | — | 1',4'-diF | F | 50-54° C. | 1.46 min | 604/606 |
| F5 | N | 2-chloro-pyrid-4-yl | —CF₃ | H | 1-F | — | F | 68-71° C. | 1.45 min | 587/589 |
| F6 | N | 2-chloro-pyrid-4-yl | —CF₃ | H | — | 1'-F | F | 148-153° C. | 1.43 min | 587/589 |
| F7 | N | 2-chloro-pyrid-4-yl | —CF₃ | H | — | 1'-Me | F | 73-77° C. | 1.48 min | 583/585 |
| F8 | N | 2-chloro-pyrid-4-yl | —CF₃ | H | — | 1'-Cl | Cl | 89-95° C. | 1.55 min | 621/633 |
| F9 | N | 2-chloro-pyrid-4-yl | —CF₃ | H | — | 1',4'-diF | F | 71-75° C. | 1.46 min | 605/607 |
| F10 | N | 2-chloro-pyrid-4-yl | —CF₃ | H | — | 2'-F | F | | 1.43 min | 670 |
| F11 | CH | 2-chloro-pyrid-4-yl | —F | H | — | 1'-F | F | | 1.50 min | 636 |
| F12 | CH | 2-chloro-pyrid-4-yl | —F | H | — | 2'-F | F | | 1.60 min | 536 |
| F13 | N | 2-chloro-pyrid-4-yl | —Cl | —Cl | — | 1'-Me | F | 122-127° C. | 1.50 min | 585/587 |
| F14 | CH | 2-chloro-pyrid-4-yl | —CF₃ | H | — | 2',3'-diCl | H | 142° C. | 1.56 min | 620-622 |
| F15 | N | 2-chloro-pyrid-4-yl | —CF₃ | H | — | 2',3'-diCl | H | 82° C. | 1.56 min | 621/623 |
| F16 | CH | 2-chloro- | —CF₃ | H | 2-F | 1'-F | Cl | 79-81° C. | 1.53 min | 620/622 |

TABLE F-continued

Compounds of formula (If)

(If)

| Comp No | A | R¹ | R³ | R⁴ | R⁶ | R⁷ | R⁸ | Physical state/ M.p. | HPLC (RT) | MS (ES+) |
|---|---|---|---|---|---|---|---|---|---|---|
| F17 | N | 2-chloro-pyrid-4-yl | —CF₃ | H | 2-F | 1'-F | Cl | 80-81° C. | 1.49 min | 621/623 |
| F18 | CH | 2-chloro-pyrid-4-yl | —CF₃ | F | 2-F | 1'-F | Cl | 79-81° C. | 1.56 min | 638/640 |
| F19 | CH | 2-chloro-pyrid-4-yl | —CF₃ | H | 2-F | 1'-F | F | 70-72° C. | 1.46 min | 604/606 |
| F20 | N | 2-chloro-pyrid-4-yl | —CF₃ | H | 2-F | 1'-F | F | 73-74° C. | 1.43 min | 605/607 |
| F21 | CH | 2-chloro-pyrid-4-yl | —CF₃ | F | 2-F | 1'-F | F | 81-83° C. | 1.51 min | 622/624 |

EXAMPLE 25

This example illustrates the preparation of 2-chloro-N-{3,4,5-trifluoro-2-[1-(4'-fluoro-biphenyl-4-ylmethyl)-piperidin-4-yl]-phenyl}-isonicotinamide N-oxide (Compound G1 of Table G).

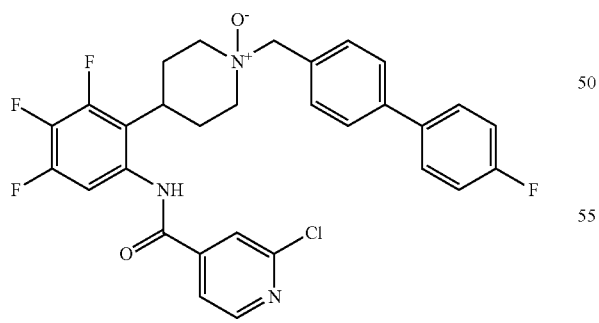

The title compound was prepared from 2-chloro-N-{3,4,5-trifluoro-2-[1-(4'-fluoro-biphenyl-4-ylmethyl)-piperidin-4-yl]-phenyl}-isonicotinamide (Compound E1 of Table E) as described in Example 2.

The following compounds were prepared according to procedures analogous to the procedure described in Example 25:

TABLE G

Compounds of formula (Ig)

(Ig)

| Comp No | R¹ | R² | R⁴ | R⁵ | R⁸ | Physical state/ M.p. | HPLC (RT) | MS (ES+) |
|---|---|---|---|---|---|---|---|---|
| G1 | 2-chloro-pyrid-4-yl | F | F | H | F | 164-168° C. | 1.46 min | 570/572 |
| G2 | 2-chloro-pyrid-4-yl | —CF₃ | F | H | F | 187-191° C. | 1.54 min | 620/622 |
| G3 | 2-chloro-pyrid-4-yl | H | H | H | F | 203-207° C. | 1.39 min | 534/536 |
| G4 | 2-chloro-pyrid-4-yl | Cl | H | H | F | 188° C. decomposition | 1.45 min | 568/570/572 |
| G5 | 2-chloro-pyrid-4-yl | Br | H | H | F | 188° C. decomposition | 1.47 min | 612/614/616 |
| G6 | 2-chloro-pyrid-4-yl | —CF₃ | H | H | F | 185-190° C. | 1.50 min | 602/604 |
| G7 | 2-chloro-pyrid-4-yl | F | H | H | F | 185° C. decomposition | 1.39 min | 552/554 |
| G8 | 2-chloro-pyrid-4-yl | —CN | H | H | F | solid | 1.38 min | 559/561 |
| G9 | 2-chloro-pyrid-4-yl | cyclo-propyl | H | H | F | 186-191 | 1.53 min | 574/576 |

EXAMPLE 26

This example illustrates the preparation of 2-chloro-N-{3-trifluoromethyl-2-[1-(4'-chloro-biphenyl-4-ylmethyl)-piperidin-4-yl]-phenyl}-isonicotinamide N-oxide (Compound H1 of Table H).

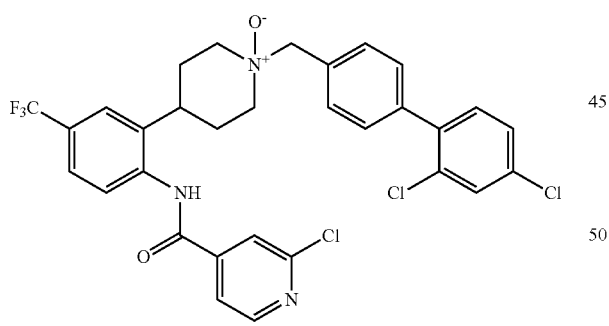

The title compound was prepared from 2-chloro-N-{3-trifluoromethyl-2-[1-(4'-chloro-biphenyl-4-ylmethyl)-piperidin-4-yl]-phenyl}-isonicotinamide (Compound F1 of Table F) as described in Example 2.

The following compounds were prepared according to procedures analogous to the procedure described in Example 26:

TABLE H

Compounds of formula (Ih)

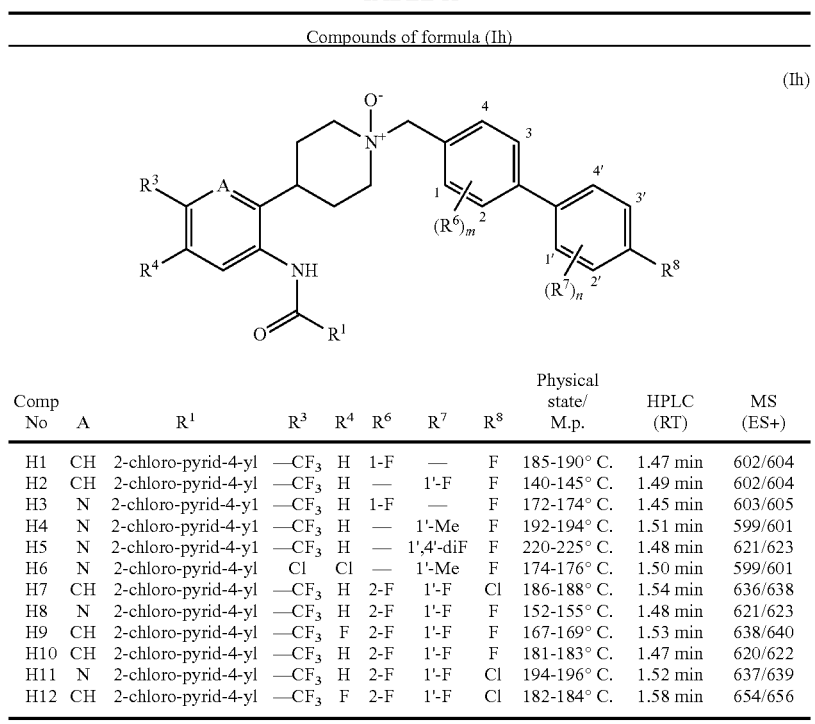

| Comp No | A | R¹ | R³ | R⁴ | R⁶ | R⁷ | R⁸ | Physical state/ M.p. | HPLC (RT) | MS (ES+) |
|---|---|---|---|---|---|---|---|---|---|---|
| H1 | CH | 2-chloro-pyrid-4-yl | —CF₃ | H | 1-F | — | F | 185-190° C. | 1.47 min | 602/604 |
| H2 | CH | 2-chloro-pyrid-4-yl | —CF₃ | H | — | 1'-F | F | 140-145° C. | 1.49 min | 602/604 |
| H3 | N | 2-chloro-pyrid-4-yl | —CF₃ | H | 1-F | — | F | 172-174° C. | 1.45 min | 603/605 |
| H4 | N | 2-chloro-pyrid-4-yl | —CF₃ | H | — | 1'-Me | F | 192-194° C. | 1.51 min | 599/601 |
| H5 | N | 2-chloro-pyrid-4-yl | —CF₃ | H | — | 1',4'-diF | F | 220-225° C. | 1.48 min | 621/623 |
| H6 | N | 2-chloro-pyrid-4-yl | Cl | Cl | — | 1'-Me | F | 174-176° C. | 1.50 min | 599/601 |
| H7 | CH | 2-chloro-pyrid-4-yl | —CF₃ | H | 2-F | 1'-F | Cl | 186-188° C. | 1.54 min | 636/638 |
| H8 | N | 2-chloro-pyrid-4-yl | —CF₃ | H | 2-F | 1'-F | F | 152-155° C. | 1.48 min | 621/623 |
| H9 | CH | 2-chloro-pyrid-4-yl | —CF₃ | F | 2-F | 1'-F | F | 167-169° C. | 1.53 min | 638/640 |
| H10 | CH | 2-chloro-pyrid-4-yl | —CF₃ | H | 2-F | 1'-F | F | 181-183° C. | 1.47 min | 620/622 |
| H11 | N | 2-chloro-pyrid-4-yl | —CF₃ | H | 2-F | 1'-F | Cl | 194-196° C. | 1.52 min | 637/639 |
| H12 | CH | 2-chloro-pyrid-4-yl | —CF₃ | F | 2-F | 1'-F | Cl | 182-184° C. | 1.58 min | 654/656 |

EXAMPLE 27

This example illustrates the preparation of 2-chloro-N-{3-trifluoromethyl-2-[1-(4'-chloro-biphenyl-4-ylmethyl)-piperidin-4-yl]-phenyl}-isonicotinamide N-oxide 3-hydroxypropyl sulfonate salt (Compound J1 of Table J).

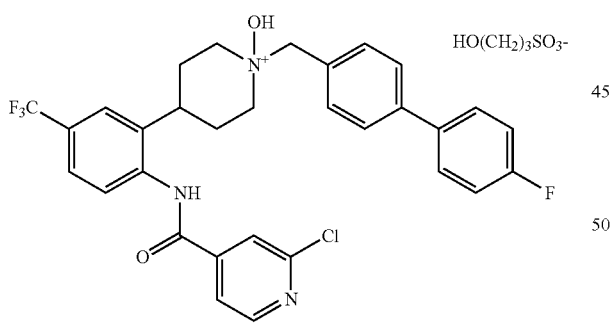

The title compound was prepared from 2-chloro-N-{3-trifluoromethyl-2-[1-(4'-chloro-biphenyl-4-ylmethyl)-piperidin-4-yl]-phenyl}-isonicotinamide N-oxide (Compound B6 of Table B) as described in Example 28.

The following compounds were prepared according to procedures analogous to the procedure described in Example 27:

TABLE J

Compounds of formula (Ij)

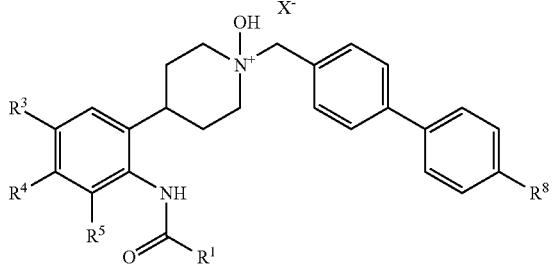

| Comp No | R¹ | R³ | R⁴ | R⁵ | R⁸ | HX | M.p. |
|---|---|---|---|---|---|---|---|
| J1 | 2-chloro-pyrid-4-yl | —CF₃ | H | H | F | HO(CH₂)₃SO₃H | 178-182° C. |
| J2 | 2-chloro-pyrid-4-yl | —CF₃ | H | H | F | H₃PO₄ | 173-175° C. |
| J3 | 2-chloro-pyrid-4-yl | —CF₃ | H | H | F | CF₃COOH | 158-161° C. |
| J4 | 2-chloro-pyrid-4-yl | —CF₃ | H | H | F | HCl | 179-180° C. |
| J5 | 2-chloro-pyrid-4-yl | —CF₃ | H | H | F | 4-CH₃—Ph—SO₃H | 168-170° C. |
| J6 | 2-chloro-pyrid-4-yl | —CF₃ | H | H | F | CH₃SO₃H | 105-107° C. |
| J7 | 2-chloro-pyrid-4-yl | —CF₃ | H | H | F | CH₃(CH₂)₃SO₃H | — |

EXAMPLE 28

This example illustrates the preparation of 2-chloro-N-[1'-(4'-fluoro-biphenyl-4-ylmethyl)-1'-oxy-6-trifluoromethyl-1',2',3',4',5',6'-hexahydro-[2,4]bipyridinyl-3-yl]-isonicotinamide 3-hydroxypropyl sulfonate salt (Compound K1 of Table K).

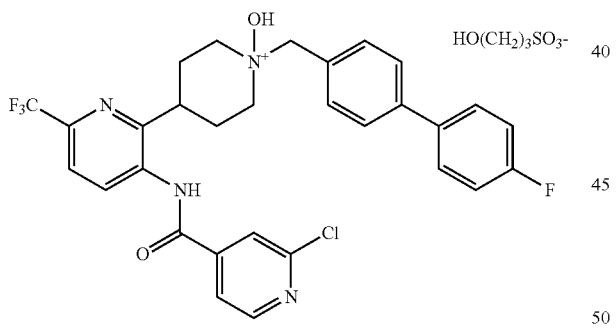

To a suspension of 2-chloro-N-[1'-(4'-fluoro-biphenyl-4-ylmethyl)-1'-oxy-6-trifluoromethyl-1',2',3',4',5',6'-hexahydro-[2,4]bipyridinyl-3-yl]-isonicotinamide (0.4 g, Compound D1 of Table D) in dichloromethane (12 ml) was added 3-hydroxypropane-1-sulfonic acid (0.14 ml). The reaction mixture was stirred for 16 hours at ambient temperature. Diethyl ether was added and the white solid isolated by filtration, washed with cold methanol and dried in high vacuum to afford the title compound (0.36 g).

The following compounds were prepared according to procedures analogous to the procedure described in Example 28:

TABLE K

Compounds of formula (Ik)

(Ik)

[Structure diagram of formula Ik]

| Comp No | R¹ | R³ | R⁴ | R⁵ | R⁸ | HX | M.p. |
|---|---|---|---|---|---|---|---|
| K1 | 2-chloro-pyrid-4-yl | —CF₃ | H | H | F | HO(CH₂)₃SO₃H | 225-230° C. |
| K2 | 2-chloro-pyrid-4-yl | —CF₃ | H | H | F | CH₃SO₃H | 195-196° C. |
| K3 | 2-chloro-pyrid-4-yl | —CF₃ | H | H | F | CH₃CH₂SO₃H | 222-224° C. |
| K4 | 2-chloro-pyrid-4-yl | —CF₃ | H | H | F | 4-CH₃—Ph—SO₃H | 256-257° C. |

EXAMPLE 29

This example illustrates the preparation of 2-chloro-N-[5,6-dichloro-1'-(4'-fluoro-biphenyl-4-ylmethyl)-1'-oxy-1',2',3',4',5',6'-hexahydro-[2,4]bipyridinyl-3-yl]-isonicotinamide hydrochloride (Compound M1 of Table M).

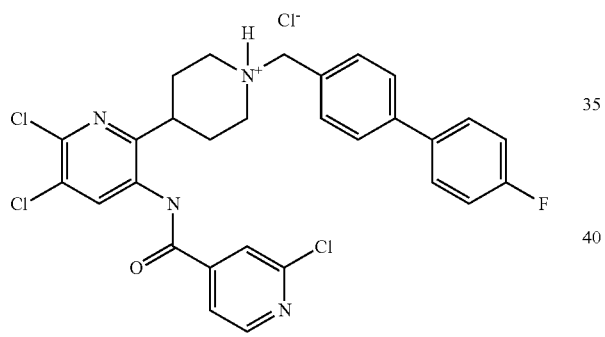

To a suspension 2-chloro-N-[5,6-dichloro-1'-(4'-fluoro-biphenyl-4-ylmethyl)-1'-oxy-1',2',3',4',5',6'-hexahydro-[2,4]bipyridinyl-3-yl]-isonicotinamide (0.15 g, Compound C2 of Table C) in dichloromethane (1 ml) was added concentrated hydrochloric acid (0.05 g). The precipitate was isolated by filtration and dried under high vacuum to yield the title compound.

The following compounds were prepared according to procedures analogous to the procedure described in Example 29:

TABLE M

Compounds of formula (Im)

(Im)

[Structure diagram of formula Im]

| Comp No | R¹ | R³ | R⁴ | R⁵ | R⁸ | HX | M.p. |
|---|---|---|---|---|---|---|---|
| M1 | 2-chloro-pyrid-4-yl | —Cl | —Cl | H | F | HCl | 240° C. |
| M2 | 2-chloro-pyrid-4-yl | —Cl | —Cl | H | F | 3-PhO—(CH₂)₂CO₂H | 75-80° C. |
| M3 | 2-chloro-pyrid-4-yl | —Cl | —Cl | H | F | 2-Cl—Ph—CO₂H | 195-200° C. |

TABLE M-continued

Compounds of formula (Im)

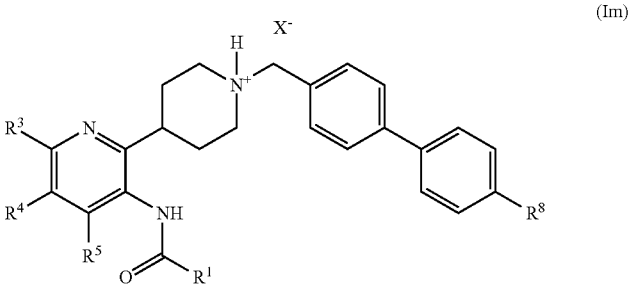

(Im)

| Comp No | R¹ | R³ | R⁴ | R⁵ | R⁸ | HX | M.p. |
|---|---|---|---|---|---|---|---|
| M4 | 2-chloro-pyrid-4-yl | —CF₃ | H | H | F | 4-CH₃—Ph—SO₃H | 246-248° C. |
| M5 | 2-chloro-pyrid-4-yl | —CF₃ | H | H | F | CH₃SO₃H | 274-275° C. |
| M6 | 2-chloro-pyrid-4-yl | —CF₃ | H | H | F | CH₃CH₂SO₃H | 278-279° C. |
| M7 | 2-chloro-pyrid-4-yl | —CF₃ | H | H | F | CH₃(CH₂)₁₁CO₂H | 130-132° C. |
| M8 | 2-chloro-pyrid-4-yl | —CF₃ | H | H | F | HO(CH₂)₃SO₃H | 288-289° C. |

BIOLOGICAL EXAMPLES

This Example illustrates the pesticidal/insecticidal properties of compounds of formula (1). The tests were performed as follows:

*Spodoptera littoralis* (Egyptian Cotton Leafworm)

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compounds gave at least 80% control of *Spodoptera littoralis*: A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, B1, B2, B3, B4, B5, B6, B7, B8, B9, B10, B11, B12, B13, B14, B15, B16, B17, B18, B19, B20, B21, B22, B23, B24, B25, B26, B27, B28, B29, C1, C2, C3, C4, C5, C6, C7, C8, C9, C10, C11, C12, C13, C14, C15, C16, C17, C18, C19, C20, C21, C22, C23, C24, C25, C26, C28, C29, C30, C31, C32, C33, C34, C35, C36, C37, C38, C39, C40, C41, C42, C43, C44, D1, D2, D3, D4, D5, D6, D7, D8, D9, D10, D11, D12, D13, D14, D15, D16, D17, D18, D19, D20, D21, D22, D23, D24, D25, D26, D27, E1, E2, E3, E4, E5, E6, E7, E8, E9, F1, F2, F4, F5, F6, F7, F8, F9, G1, G2, G3, G4, G5, G6, G7, G8, G9, H1, H2, H3, H4, H5, J1, J2, J3, J4, K1, K2, K3, K4, M1, M2, M3, M4, M5, M6, M7, M8.

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compounds gave at least 80% control of *Heliothis virescens*: A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, A36, A37, A38, A39, A40, A41, A42, A43, A44, A45, A46, B1, B2, B4, B5, B6, B7, B8, B9, B10, B11, B12, B13, B14, B15, B16, B17, B18, B20, B22, B23, B24, B25, B26, B27, B28, B29, C1, C2, C3, C4, C5, C6, C7, C8, C9, C10, C11, C12, C13, C14, C15, C16, C17, C18, C19, C20, C21, C22, C23, C24, C25, C26, C28, C29, C30, C31, C32, C34, C35, C36, C37, C38, C39, C40, C41, C42, C43, C44, D1, D2, D3, D4, D5, D6, D7, D8, D9, D10, D11, D12, D13, D14, D16, D17, D18, D19, D20, D21, D22, D23, D24, D25, D26, D27, E1, E2, E3, E4, E5, E6, E7, E8, E9, F1, F2, F3, F4, F5, F6, F8, F9, G1, G2, G3, G4, G5, G6, G7, G8, G9, H1, H2, H3, H4, H5, J1, J2, J3, J4, K1, K2, K3, K4, M1, M2, M3, M4, M5, M6, M7, M8

*Plutella xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compounds gave at least 80% control of *Plutella xylostella*: A1, A2, A3, A4, A5, A6, A7, A8, A9, A10, A11, A12, A13, A14, A15, A16, A17, A18, A19, A20, A22, A23, A24, A25, A26, A27, A28, A29, A30, A31, A32, A33, A34, A35, A36, A37, A38, A39, A40, A41, A42, A43, A44, A45, A46, B1, B2, B4, B5, B6, B7, B8, B9, B10, B11, B12, B13, B14, B16, B17, B18, B19, B20, B22, B23, B24, B25, B26, B27, B28, B29, C1, C2, C3, C4, C5, C6, C7, C8, C9, C10, C11, C12, C13, C14, C15, C16, C17, C18, C19, C20, C21, C22, C23, C24, C25, C26, C28, C29, C30, C31, C32, C33, C34, C35, C36, C37, C38, C39, C40, C41, C42, C43, C44, D1, D2, D3, D4, D5, D6, D7, D8, D9, D10, D11, D12, D13, D14, D15, D16, D17, D18, D19, D20, D21, D22, D23, D24, D25, D26, D27, E1, E2, E3, E4, E5, E6, E7, E8, E9, F1, F2, F4, F5, F6, F7, F8, F9, G1, G2, G3, G4, G5, G6, G7, G8, G9, H1, H2, H3, H4, H5, J1, J2, J3, J4, K1, K2, K3, K4, M1, M2, M3, M4, M5, M6, M7, M8

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with larvae (L2) (6-10 per well). After an incubation period of 5 days, samples were checked for larval mortality, and growth regulation.

The following compounds gave at least 80% control of *Diabrotica balteata*: A1, A2, A3, A4, A5, A6, A7, A8, A9, A10, A11, A12, A13, A14, A15, A16, A17, A18, A19, A20, A22, A23, A24, A25, A26, A27, A28, A29, A30, A31, A32, A33, A34, A35, A37, A38, A39, A40, A41, A42, A43, A44, A45, B1, B2, B4, B5, B6, B7, B8, B9, B10, B11, B12, B13, B14, B15, B16, B17, B18, B20, B21, B22, B23, B24, B25, B26, B27, B29, C1, C2, C3, C4, C5, C6, C7, C8, C9, C10, C11, C12, C13, C14, C15, C16, C17, C18, C19, C20, C21, C22, C23, C24, C25, C26, C28, C29, C30, C31, C32, C33, C34, C36, C37, C38, C39, C40, C41, C42, C43, C44, D1, D2, D3, D4, D5, D6, D7, D8, D9, D10, D11, D12, D13, D14, D16, D17, D18, D19, D20, D21, D22, D23, D24, D25, D26, E1, E2, E3, E4, E5, E6, E7, E8, E9, F1, F2, F3, F4, F5, F6, F8, F9, G1, G2, G3, G4, G5, G6, G7, G8, H1, H2, H3, J1, J2, J3, J4, K1, K2, K3, K4, M1, M3, M4, M5, M6, M7, M8

*Aedes aegypti* (Yellow Fever Mosquito):

10-15 *Aedes* larvae (L2) together with a nutrition mixture are placed in 96-well microtiter plates. Test solutions at an application rate of 2 ppm were pipetted into the wells. 2 days later, insects were checked for mortality and growth inhibition.

The following compounds gave at least 80% control of *Aedes aegypti*: A1, A2, A3, A4, A5, B1, B2, B4, C1, C2, C3, C4, C5, D1.

The invention claimed is:

1. A compound of formula (I):

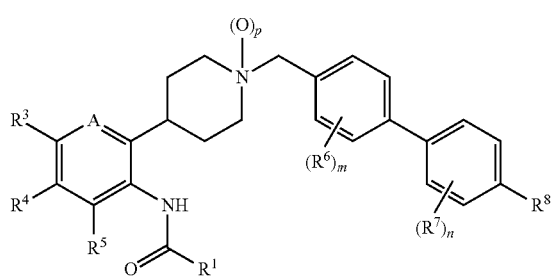

wherein
A is N;
p is 0 or 1;
$R^1$ is pyrid-4-yl optionally substituted by one or two substituents each independently selected from halogen, $C_1$-$C_3$alkyl or $C_1$-$C_3$haloalkyl;
$R^3$ and $R^4$ are each independently hydrogen, halogen, cyano, $C_1$-$C_8$alkyl, $C_1$-$C_8$haloalkyl, $C_2$-$C_8$alkenyl, $C_2$-$C_8$haloalkenyl, $C_3$-$C_8$cycloalkyl, $C_3$-$C_8$halocycloalkyl, $C_1$-$C_8$alkoxy, $C_1$-$C_8$haloalkoxy, $C_1$-$C_8$alkylthio or $C_1$-$C_8$haloalkylthio;
$R^5$ is hydrogen or halogen;
each $R^6$ and $R^7$ is independently halogen, $C_1$-$C_8$alkyl, $C_1$-$C_8$haloalkyl, $C_1$-$C_8$alkoxy or $C_1$-$C_8$haloalkoxy;
m is 0, 1 or 2;
n is 0, 1 or 2; and
$R^8$ is hydrogen, halogen, cyano, $C_1$-$C_8$alkyl, $C_1$-$C_8$haloalkyl, $C_3$-$C_8$cycloalkyl, $C_2$-$C_8$alkenyl, $C_2$-$C_8$haloalkenyl, $C_2$-$C_8$alkynyl, $C_1$-$C_8$alkoxy or $C_1$-$C_8$haloalkoxy;
or a salt thereof.

2. A compound according to claim 1 wherein $R^1$ is pyrid-4-yl optionally substituted by one or two substituents each independently selected from fluoro, chloro, bromo, methyl, difluoromethyl, chlorodifluoromethyl or trifluoromethyl.

3. A compound according to claim 1 wherein $R^3$ is hydrogen, halogen, cyano, $C_1$-$C_6$alkyl, $C_1$-$C_6$haloalkyl, $C_2$-$C_6$alkenyl, $C_3$-$C_6$ cycloalkyl, $C_1$-$C_6$ alkoxy, $C_1$-$C_6$haloalkoxy, $C_1$-$C_6$alkylthio or $C_1$-$C_6$haloalkylthio.

4. A compound according to claim 1 wherein $R^4$ is hydrogen, halogen, cyano, $C_1$-$C_6$ alkyl, $C_1$-$C_6$haloalkyl, $C_2$-$C_6$alkenyl, $C_3$-$C_6$ cycloalkyl, $C_1$-$C_6$alkoxy, $C_1$-$C_6$haloalkoxy, $C_1$-$C_6$ alkylthio or $C_1$-$C_6$haloalkylthio.

5. A compound according to claim 1 wherein $R^5$ is hydrogen, fluoro, chloro or bromo.

6. A compound according to claim 1 wherein each $R^6$ is independently halogen, $C_1$-$C_6$alkyl or $C_1$-$C_6$alkoxy.

7. A compound according to claim 1 wherein m is 0 or 1.

8. A compound according to claim 1 wherein each $R^7$ is independently halogen, $C_1$-$C_6$alkyl or $C_1$-$C_6$alkoxy.

9. A compound according to claim 1 wherein n is 0 or 1.

10. A compound according to claim 1 wherein $R^8$ is hydrogen, halogen, cyano, $C_1$-$C_6$alkyl, $C_1$-$C_6$haloalkyl, $C_3$-$C_6$cycloalkyl, $C_2$-$C_6$alkenyl, $C_2$-$C_6$haloalkenyl, $C_2$-$C_6$ alkynyl, $C_1$-$C_6$alkoxy or $C_1$-$C_6$haloalkoxy.

11. A compound according to claim 1 wherein:
$R^1$ is pyrid-4-yl optionally substituted by one or two substituents each independently selected from fluoro, chloro, bromo, methyl, difluoromethyl, chlorodifluoromethyl or trifluoromethyl;
$R^3$ is hydrogen, halogen, cyano, $C_1$-$C_6$alkyl, $C_1$-$C_6$haloalkyl, $C_2$-$C_6$alkenyl, $C_3$-$C_6$cycloalkyl, $C_1$-$C_6$alkoxy, $C_1$-$C_6$haloalkoxy, $C_1$-$C_6$alkylthio or $C_1$-$C_6$haloalkylthio;
$R^4$ is hydrogen, halogen, cyano, $C_1$-$C_6$alkyl, $C_1$-$C_6$haloalkyl, $C_2$-$C_6$alkenyl, $C_3$-$C_6$cycloalkyl, $C_1$-$C_6$alkoxy, $C_1$-$C_6$haloalkoxy, $C_1$-$C_6$alkylthio or $C_1$-$C_6$haloalkylthio;
$R^5$ is hydrogen, fluoro, chloro or bromo;
each $R^6$ is independently halogen, $C_1$-$C_6$alkyl or $C_1$-$C_6$alkoxy;
m is 0 or 1;
each $R^7$ is independently halogen, $C_1$-$C_6$alkyl or $C_1$-$C_6$alkoxy;
n is 0 or 1; and
$R^8$ is hydrogen, halogen, cyano, $C_1$-$C_6$alkyl, $C_1$-$C_6$haloalkyl, $C_3$-$C_6$cycloalkyl, $C_2$-$C_6$alkenyl, $C_2$-$C_6$haloalkenyl, $C_2$-$C_6$alkynyl, $C_1$-$C_6$alkoxy or $C_1$-$C_6$haloalkoxy.

12. A compound according to claim 1 wherein at least one of m and n is 0.

13. A compound according to claim 1 wherein each of m and n is 0.

14. A compound according to claim 1 wherein p is 0.

15. A compound according to claim 2 wherein $R^1$ is pyrid-4-yl optionally substituted by one or two substituents each independently selected from fluoro, chloro and methyl.

16. A compound according to claim 15 wherein $R^5$ is hydrogen, fluoro, chloro or bromo.

17. An insecticidal composition comprising an insecticidally effective amount of a compound of claim 1.

18. An insecticidal composition comprising an insecticidally effective amount of a compound of claim 16.

19. An insecticidal composition comprising an insecticidally effective amount of a compound of claim 15.

20. A method of combating and controlling insects which comprises applying to a pest, to a locus of a pest, or to a plant susceptible to attack by a pest an insecticidally effective amount of a compound of claim 1.

* * * * *